(12) United States Patent
Dorvillius et al.

(10) Patent No.: US 10,669,328 B2
(45) Date of Patent: *Jun. 2, 2020

(54) HUMAN IGG1 DERIVED ANTIBODY WITH PRO-APOPTOTIC ACTIVITY

(71) Applicant: OGD2 Pharma, Nantes (FR)

(72) Inventors: Mylene Dorvillius, Nantes (FR); Jean-Marc Le Doussal, Lausanne (CH); Mickael Terme, Nantes (FR)

(73) Assignee: OGD2 PHARMA, Nantes (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/036,118

(22) PCT Filed: Nov. 11, 2014

(86) PCT No.: PCT/EP2014/003011
§ 371 (c)(1),
(2) Date: May 12, 2016

(87) PCT Pub. No.: WO2015/070972
PCT Pub. Date: May 21, 2015

(65) Prior Publication Data
US 2016/0280765 A1    Sep. 29, 2016

Related U.S. Application Data

(60) Provisional application No. 61/902,926, filed on Nov. 12, 2013.

(51) Int. Cl.
| C07K 16/00 | (2006.01) |
|---|---|
| C07K 16/32 | (2006.01) |
| C07K 16/28 | (2006.01) |
| C07K 16/30 | (2006.01) |
| A61K 39/00 | (2006.01) |

(52) U.S. Cl.
CPC .......... *C07K 16/00* (2013.01); *C07K 16/2887* (2013.01); *C07K 16/3084* (2013.01); *C07K 16/32* (2013.01); *A61K 2039/505* (2013.01); *C07K 2317/24* (2013.01); *C07K 2317/522* (2013.01); *C07K 2317/53* (2013.01); *C07K 2317/72* (2013.01); *C07K 2317/73* (2013.01); *C07K 2317/92* (2013.01)

(58) Field of Classification Search
CPC .............. C07K 16/00; C07K 16/3084; C07K 2317/24; C07K 2317/52; C07K 2317/72; C07K 2317/73
USPC .......................................... 424/133.1, 178.1
See application file for complete search history.

(56) References Cited

U.S. PATENT DOCUMENTS

| 5,225,539 A | 7/1993 | Winter |
|---|---|---|
| 5,558,864 A | 9/1996 | Bendig et al. |
| 5,677,171 A | 10/1997 | Hudziak et al. |
| 5,736,137 A | 4/1998 | Anderson et al. |
| 5,821,337 A | 10/1998 | Carter et al. |
| 7,060,808 B1 | 6/2006 | Goldstein et al. |
| 2010/0150910 A1 | 6/2010 | Birkle et al. |
| 2012/0022238 A1 | 1/2012 | Shitara et al. |
| 2016/0272722 A1* | 9/2016 | Le Doussal ........ C07K 16/3084 |

FOREIGN PATENT DOCUMENTS

| GB | 2188638 A | 10/1967 |
|---|---|---|
| WO | 2004/035607 A2 | 4/2004 |
| WO | 20050070967 A2 | 8/2005 |
| WO | 2008/043777 A1 | 4/2008 |
| WO | 2012/035141 A1 | 3/2012 |

OTHER PUBLICATIONS

Hovenden et al. PLoS Pathog 9(4): e1003306 (Apr. 2013).*
Terme et al. PLoS One 9(2): e87210 (Feb. 2014).*
Akito Natsume et al.: "Engineered Antibodies of IgG1/IgG3 Mixed Isotype with Enhanced Cytotoxic Activities", Cancer Research, American Association for Cancer Research, US, vol. 68, No. 10, May 15, 2008 (May 15, 2008), pp. 3863-3872, XP007913550, ISSN: 0008-5472, DOI: 10.115810008-5472.CAN-07-6297.
Chappel M S et al.: "Identification of the FC-Gamma Receptor Class I Binding Site in Human IGG Through the Use of Recombinant IGG1-IGG2 Hybrid and Point-Mutated Antibodies", Proceedings of the National Academy of Sciences, National Academy of Sciences, US, vol. 88, No. 20, Oct. 1, 1991 (Oct. 1, 1991), pp. 9036-9040, XP002392092, ISSN: 0027-8424, DOI: 10.1073/PNAS.88.20.9036.
Dorai H et al.: "Role of inter-heavy and light chain disulfide bonds in the effector functions of human immunoglobulin IgG1", Molecular Immunology, Pergamon, GB, vol. 29, No. 12, Dec. 1, 1992 (Dec. 1, 1992), pp. 1487-1491, XP023683059, ISSN: 0161-5890, DOI: 10.1016/0161-5890(92)90222-J.

(Continued)

*Primary Examiner* — Lynn A Bristol
(74) *Attorney, Agent, or Firm* — Young & Thompson

(57) ABSTRACT

A method for increasing the therapeutic efficacy of a human immunoglobulin G class 1 (IgG1) antibody, includes: mutating the human CH1γ1 domain from the antibody, to restore the pairing between CH1 and CL domains that is typical of the other IgG subclasses, or by substituting the human CH1γ1 domain by the CH1 domain from a human IgG2 (CH1γ2), IgG3 (CH1γ3) or IgG4 (CH1γ4); the antibody obtained by such method, includes a) a light chain including the following amino acid sequences: i) the Light Chain Variable Region (LCVR) specific from an antigen; and ii) a human kappa (κ)Constant (CL) domain; and b) a heavy chain including the following amino acid sequences: i) the Heavy Chain Variable Region (HCVR) specific from the antigen; ii) the CH2 and CH3 domains from a human IgG1; and iii) the CH1 domain from a human IgG1, mutated to restore pairing between CHI and CL domains.

25 Claims, 5 Drawing Sheets

Specification includes a Sequence Listing.

(56) References Cited

OTHER PUBLICATIONS

James T. Heads et al.: "Relative stabilities of IgG1 and IgG4 Fab domains: Influence of the light-heavy interchain disulfide bond architecture", Protein Science, vol. 21, No. 9, Aug. 9, 2012 (Aug. 9, 2012), pp. 1315-1322, XP055068243, ISSN: 0961-8368, DOI: 10.1002/pro.2118.
Ludwig D L et al.: "Monoclonal Antibody Therapeutics and Apoptosis", Oncogene, Nature Publishing Group, GB, vol. 22, No. 56, Dec. 8, 2003 (Dec. 8, 2003), pp. 9097-9106, XP008050059, ISSN: 0950-9232, DOI: 10.1038/SJ.ONC.1207104.
S Yoshida et al.: "Ganglioside G(D2) in small cell lung cancer cell lines: enhancement of cell proliferation and mediation of apoptosis", Cancer Research, May 15, 2001 (May 15, 2001), United States, pp. 4244-4252, XP055177738, Retrieved from the Internet <URL:http://cancerres.aacrjournals.org/content/61/10/4244.full.pdf> [retrieved on Feb. 19, 2015].
International Search Report, dated Apr. 2, 2015, from corresponding PCT application.
Liu Hongcheng et al., "Disulfide bond structures of IgG molecules", Landes Bioscience, Jan./Feb. 2012, 4:1, pp. 17-23.
Jennifer Konitzer et al., "Reformatting Rituximab into Human IgG2 and IgG4 Isotypes Dramatically Improves Apoptosis Induction In Vitro", PLOS ONE, Dec. 2015, 29:10, DOI:10.1371/journal.pone.0145633, pp. 1-20.

\* cited by examiner

Light chain sequence: SEQ ID NO: 12

```
    VL
   ┌──►                  20                    40                    60
   DVVMTQTPLS  LPVSLGDQAS  ISCRSSQSLL  KNNGNTFLHW  YLQKSGQSPK  LLIYKVSNRL
                          80                   100                   120
                                                                        Ck
                                                                       ┌──►
   SGVPDRFSGS  GSGTYFTLKI  SRVEAEDLGV  YFCSQSTHIP  YTFGGGTKLE  I RTVAAPSV
                         140                   160                   180
   FIFPPSDEQL  KSGTASVVCL  LNNFYPREAK  VQWKVDNALQ  SGNSQESVTE  QDSKDSTYSL
                         200
   SSTLTLSKAD  YEKHKVYACE  VTHQGLSSPV  TKSFNRGEC
```

Heavy chain sequence: SEQ ID NO: 13

```
    VH
   ┌──►                  20                    40                    60
   EVKLVESGGG  LVLPGDSLRL  SCATSEFTFT  DYYMTWVRQP  PRKALEWLGF  IRNRANGYTT
                          80                   100                   120
                                                                        CH1
                                                                       ┌──►
   EYNPSVKGRF  TISRDNSQSI  LYLQMNTLRT  EDSATYYCAR  VSNWAFDYWG  QGTTLTVSSA
                         140                   160                   180
   STKGPSVFPL  APSSKSTSGG  TAALGCLVKD  YFPEPVTVSW  NSGALTSGVH  TFPAVLQSSG
                         200                        Hinge                 CH2
                                                   ┌──►                  ┌──►
   LYSLSSVVTV  PSSSLGTQTY  ICNVNHKPSN  TKVDKKV EPK  SCDKTHTCPP  C APELLGGP
                         260                   280                   300
   SVFLFPPKPK  DTLMISRTPE  VTCVVVDVSH  EDPEVKFNWY  VDGVEVHNAK  TKPREEQYNS
                         320                        CH3
                                                   ┌──►
   TYRVVSVLTV  LHQDWLNGKE  YKCKVSNKAL  PAPIEKTISK  A GQPREPQV  YTLPPSREEM
                         380                   400                   420
   TKNQVSLTCL  VKGFYPSDIA  VEWESNGQPE  NNYKTTPPVL  DSDGSFFLYS  KLTVDKSRWQ
                         440
   QGNVFSCSVM  HEALHNHYTQ  KSLSLSPGK
```

Figure 1

```
ASTKGPSVFP LAPCSKSTSG GTAALGCLVK DYFPEPVTVS WNSGALTSGV HTFPAVLQSS
GLYSLSSVVT VPSSSLGTQT YICNVNHKPS NTKVDKKV EPKSCDKTHTCPPCP APELLGGP
```

Figure 2 (SEQ ID NO :14)

```
ASTKGPSVFP LAPCSKSTSG GTAALGCLVK DYFPEPVTVS WNSGALTSGV HTFPAVLQSS
GLYSLSSVVT VPSSSLGTQT YICNVNHKPS NTKVDKKV EPKSSDKTHTCPPC PAPELLGGP
```

Figure 3 (SEQ ID NO :15)

```
ASTKGPSVFP LAPCSRSTSG GTAALGCLVK DYFPEPVTVS WNSGALTSGV HTFPAVLQSS
GLYSLSSVVT VPSSSLGTQT YTCNVNHKPS NTKVDKRV EPKSCDKTHTCPPCP APELLGGP
```

Figure 4 (SEQ ID NO :16)

```
ASTKGPSVFP LAPCSKSTSG GTAALGCLVK DYFPEPVTVS WNSGALTSGV HTFPAVLQSS
GLYSLSSVVT VPSSSLGTQT YICNVNHKPS NTKVDKKV ELKTPLGDTTHT CPRCP
EPKSCDTPPPCPRCP EPKSCDTPPPCPRCP EPKSCDTPPPCPRCP APELLGGP
```

Figure 5 (SEQ ID NO :17)

```
ASTKGPSVFP LAPCSRSTSG GTAALGCLVK DYFPEPVTVS WNSGALTSGV HTFPAVLQSS
GLYSLSSVVT VPSSSLGTQT YTCNVNHKPS NTKVDKRV ELKTPLGDTTHT
CPRCP EPKSCDTPPPCPRCP EPKSCDTPPPCPRCP EPKSCDTPPPCPRCP APELLGGP
```

Figure 6 (SEQ ID NO :18)

```
ASTKGPSVFP LAPCSKSTSG GTAALGCLVK DYFPEPVTVS WNSGALTSGV HTFPAVLQSS
GLYSLSSVVT VPSSSLGTQT YICNVNHKPS NTKVDKKV ELKTPLGDTTHT CPRCP
APELLGGP
```

Figure 7 (SEQ ID NO :19)

```
ASTKGPSVFP LAPCSRSTSG GTAALGCLVK DYFPEPVTVS WNSGALTSGV HTFPAVLQSS
GLYSLSSVVT VPSSSLGTQT YTCNVNHKPS NTKVDKRV ELKTPLGDTTHT CPRCP
APELLGGP
```

Figure 8 (SEQ ID NO :20)

ASTKGPSVFP LAPCSRSTSG GTAALGCLVK DYFPEPVTVS WNSGALTSGV HTFPAVLQSS
GLYSLSSVVT VPSSSLGTQT YTCNVNHKPS NTKVDKRV EPKSSDKTHT CPPCP

Figure 9 (SEQ ID NO :66)

ASTKGPSVFP LAPCSRSTSE STAALGCLVK DYFPEPVTVS WNSGALTSGV HTFPAVLQSS GLYSLSSVVT
VPSSNFGTQT YTCNVDHKPS NTKVDKTV EPKSCDKTHT CPPCP

Figure 10 (SEQ ID NO :23)

ASTKGPSVFP LAPCSRSTSE STAALGCLVK DYFPEPVTVS WNSGALTSGV HTFPAVLQSS GLYSLSSVVT
VPSSSLGTKT YTCNVDHKPS NTKVDKRV EPKSCDKTHT CPPCP

Figure 11 (SEQ ID NO :24)

HUMAN IGG1 DERIVED ANTIBODY WITH PRO-APOPTOTIC ACTIVITY

The present International patent application claims the priority of the provisional application U.S. 61/902,926 filed on Nov. 12, 2013, which is herein incorporated by reference.

FIELD OF THE INVENTION

The present invention provides novel antibodies and their uses in therapies.

BACKGROUND OF THE INVENTION

Since antibodies are protein molecules having high binding activity and binding specificity to a target molecule (antigen) and high stability in blood, applications thereof to diagnostic, preventive and therapeutic agents for various human diseases have been attempted. Although antibodies are generally produced by administering (immunizing) an antigen to a non-human animal, antibodies obtained from a non-human animal have an amino acid sequence specific to the species and side effects are caused due to that the antibodies are recognized as foreign substances in the human body. Accordingly, human chimeric antibodies or humanized antibodies have been prepared from antibodies of animals other than human (non-human animals) using gene recombination techniques.

The human chimeric antibodies and humanized antibodies have resolved problems possessed by non-human animal antibodies such as mouse antibodies, such as the high immunogenicity, low effector function and short blood half-life, and applications of monoclonal antibodies to pharmaceutical preparations were made possible by using them. In the Unites States, for example, a plurality of humanized antibodies has already been approved as an antibody for cancer treatment, and are on the market.

These human chimeric antibodies and humanized antibodies actually show effects to a certain degree at clinical level, but therapeutic antibodies having higher effects are in demand. For example, in the case of single administration of Rituxan (manufactured by IDEC/Roche/Genentech) which is a human chimeric antibody to CD20, it has been reported that its response ratio for recurrent low malignancy non-Hodgkin lymphoma patients in the phase III clinical test is no more than 48% (complete remission 6%, partial remission 42%), and its average duration of response is 12 months. In the case of single administration of Herceptin (manufactured by Genentech) which is a humanized antibody to HER2, it has been reported that its response ratio for metastatic breast cancer patients in the phase III clinical test is only 15%, and its average duration of response is 9.1 months.

The human antibody molecule is also called immunoglobulin (hereinafter referred to as Ig) and classified into subclasses of IgA1, IgA2, IgD, IgE, IgG1, IgG2, IgG3, IgG4 and IgM based on its molecular structure. The four human IgG isotypes (IgG1, IgG2, IgG3 and IgG4) are highly homologous with each other in the amino acid sequence in the H chain constant region except for the hinges showing a wide variety. However, these isotypes induce an effector activity of different strengths. In general, the ADCC activity decreases in the following order: IgG1>IgG3>IgG4=IgG2, while the CDC activity decreases in the following order: IgG3≥IgG1>>IgG2≈IgG4.

Although human IgG1 and human IgG3 are subclasses having excellent ADCC and CDC activities, it is known that human IgG3 antibody has a shorter half life in the blood than other human IgG subclasses and thus quickly disappears from the blood after the administration. It is also known that human IgG3 has no protein A-binding activity, differing from other human IgG subclasses. In producing an antibody on an industrial scale, a purification process using protein A is predominant and other processes using, for example, protein G have some problems such as a high purification cost.

Based on the above it can be said that human IgG1 antibody is the most suitable subclass as an antibody drug, since it has higher ADCC and CDC activities than other subclasses, can be purified using protein A, shows a long half life in blood and has a merit from the viewpoint of production cost. Although a human IgG1 antibody has been employed as drugs in practice as described above, the drug effects exhibited by the existing antibody drugs are still insufficient.

Thus, there has been required an antibody drug having improved effects.

Many modifications have been introduced in the amino acid sequence of the human IgG1 by swapping part of it. However, such an antibody prepared through the replacement of an amino acid sequence which is not present in the nature has a risk that it is recognized as a foreign matter in the human body and thus induces a side effect similar to the non-human animal antibody as discussed above. On the other hand, the amino acid sequence of an antibody prepared by swapping amino acid sequences between human subclasses is a combination of amino acid sequences of antibodies inherently carried by humans.

SUMMARY OF THE INVENTION

Now, the inventors have surprisingly shown that a specific mutation in the CH1γ1 of a chimeric antibody (c8B6), which restore the pairing between CH1 and CL domains that is typical of other IgG subclasses, or its substitution by a human CH1γ3 result in the restoration of the pro-apoptotic activity of the parent murine IgG3 8B6 antibody, said property being inherent to most of the IgG3 antibodies.

Consequently, it seems that the atypical pairing between the hinge and the CL domain in the human IgG1—because of the absence of cysteine in the CH1 domain—is associated with the lower pro-apoptotic activity observed for the IgG1 antibodies.

Consequently, the present invention relates to a method for increasing the therapeutic efficacy of a human immunoglobulin G class 1 (IgG1) antibody, derivative or a functional fragment thereof comprising the step of mutating the human CH1γ1 domain from said antibody, so as to restore the pairing between CH1 and CL domains typical of other IgG subclasses, or by substituting said human CH1γ1 domain by the CH1 domain from a human non-IgG1 subclass, such as a CH1 domain from IgG2 (CH1γ2), from IgG3 (CH1γ3) or from IgG4 (CH1γ4).

The IgG1 derived antibody obtained by the method of the present invention presents a combination of the IgG1 inherent properties and of an increased pro-apoptotic activity resulting in a potentialized therapeutic efficiency.

The present invention also relates to an antibody, or functional fragment thereof, which can be obtained by such method, wherein said antibody comprises:

a) a light chain comprising the following amino acid sequences:
  i) the Light Chain Variable Region (LCVR) specific from an antigen; and ii) a human kappa (κ) Constant (CL) domain; and b) a heavy chain comprising the following amino acid sequences:

i) the Heavy Chain Variable Region (HCVR) specific from said antigen;

ii) the CH2 and CH3 domains from a human IgG1; and iii) the CH1 domain from a human IgG1, which is mutated so as to restore the pairing between CH1 and CL domains that is typical of other IgG subclasses, or is substituted by a CH1 domain from a human IgG2, IgG3 or IgG4.

The present invention also relates to a pharmaceutical composition comprising at least one of such antibody, and a pharmaceutically acceptable carrier.

Additionally, the present invention relates to a method for treating a cancer comprising providing to a patient in need thereof such a pharmaceutical composition which comprises at least one said antibody, or at least one functional fragment thereof.

Finally, the present invention relates to the use of at least one of such antibody, or of at least one functional fragment thereof for the preparation of a medicament for treating and/or preventing cancer.

BRIEF DESCRIPTION OF THE FIGURES

FIG. 1 shows the light (SEQ ID NO:12) and heavy (SEQ ID NO:13) chain sequences of the c8B6 antibody.

FIG. 2 shows the CH1 and hinge domains sequence of the 301.14a antibody (SEQ ID NO: 14).

FIG. 3 shows the CH1 and hinge domains sequence of the 301.14b and 311.14b antibodies (SEQ ID NO: 15).

FIG. 4 shows the CH1 and hinge domains sequence of the 301.15 and 311.15 antibodies (SEQ ID NO: 16).

FIG. 5 shows the CH1 and hinge domains sequence of the 301.16 antibody ((SEQ ID NO:17).

FIG. 6 shows the CH1 and hinge domains sequence of the 301.17 antibody (SEQ ID NO: 18).

FIG. 7 shows the CH1 and hinge domains sequence of the 301.18 antibody ((SEQ ID NO:19).

FIG. 8 shows the CH1 and hinge domains sequence of the 301.19 antibody (SEQ ID NO:20).

FIG. 9 shows the CH1 and hinge domains sequence of the 301.15b antibody (SEQ ID NO:66).

FIG. 10 shows the CH1 and hinge domains sequence of the 301.20 antibody (SEQ ID NO:23).

FIG. 11 shows the CH1 and hinge domains sequence of the 301.21 antibody (SEQ ID NO:24).

DETAILED DESCRIPTION

Figure 12:
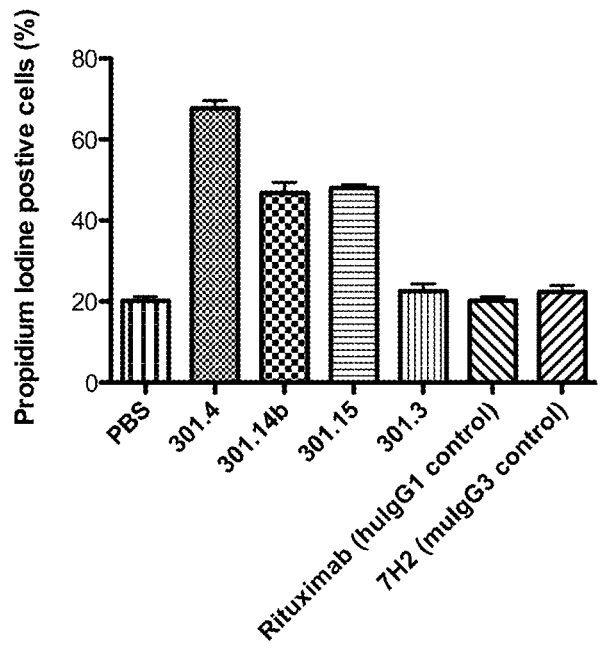
FIG. 12 shows the direct cytotoxicity of anti-OacGD2 antibodies by propidium iodide.

In a first aspect, the present invention concerns a method for increasing the therapeutic efficacy of a human immunoglobulin G class 1 (IgG1) antibody, derivative or a functional fragment thereof comprising the step of mutating the human CH1γ1 domain from said antibody, so as to restore the pairing between CH1 and CL domains that is typical of other IgG subclasses, or by substituting said human CH1γ1 domain by the CH1 domain from a human IgG2 (CH1γ2), IgG3 (CH1γ3) or IgG4 (CH1γ4).

Said method of increasing the therapeutic efficiency comprises increasing the pro-apoptotic activity of said antibody.

An antibody is an immunoglobulin molecule corresponding to a tetramer comprising four polypeptide chains, two identical heavy (H) chains (about 50-70 kDa when full length) and two identical light (L) chains (about 25 kDa when full length) inter-connected by disulfide bonds. Light chains are classified as kappa and lambda.

The heavy chain is classified as gamma for the IgG. Each heavy chain is comprised of a N-term heavy chain variable region (abbreviated herein as HCVR) and a heavy chain constant region. The heavy chain constant region is comprised of three domains (CH1, CH2, and CH3) for IgG and a hinge domain between CH1 and CH2 domains.

Each light chain is comprised of a N-term light chain variable region (abbreviated herein as LCVR) and a light chain constant region. The light chain constant region is comprised of one domain, CL. The HCVR and LCVR regions can be further subdivided into regions of hypervariability, termed complementarity determining regions (CDRs), interspersed with regions that are more conserved, termed framework regions (FR). Each HCVR and LCVR is composed of three CDRs and four FRs, arranged from amino-terminus to carboxy-terminus in the following order: FR1, CDR1, FR2, CDR2, FR3, CDR3, FR4. The assignment of amino acids to each domain is in accordance with well-known conventions (IMGT, The International Immunogenetics Information System®, LEFRANC et al., *Nucleic Acids Research*, vol. 27, p: 209-212, 1999). The functional ability of the antibody to bind a particular antigen depends on the variable regions of each light/heavy chain pair, and is largely determined by the CDRs.

As used herein, the expression "derivative of a human immunoglobulin G class 1 (IgG1) antibody" refers to a chimeric or humanized antibody. Such derivative antibody comprising:

i) the light chain constant domain (CL) and the heavy chain constant domains (CH1, CH2 and CH3) from a human IgG1; and ii) the Light Chain Variable Region (LCVR) and the Heavy Chain Variable Region (HCVR), or the corresponding CDRs, not from a human IgG1.

The term "functional fragments" as used herein refers to antibody fragments, which bind specifically to the O-acetylated-GD2 ganglioside and which comprise a CH1 domain. Such fragments can be simply identified by the skilled person and comprise, as an example, $F_{ab}$ fragment (e.g., by papain digestion), $F_{ab}'$ fragment (e.g., by pepsin digestion and partial reduction), $F(_{ab}')_2$ fragment (e.g., by pepsin digestion), $F_{acb}$ (e.g., by plasmin digestion), and also $F_d$ (e.g., by pepsin digestion, partial reduction and reaggregation) fragment are encompassed by the invention.

Such fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a $F(_{ab}')_2$ heavy chain portion can be designed to include DNA sequences encoding the $CH_1$ domain and/or hinge region of the heavy chain. The various portions of antibodies can be joined together chemically by conventional techniques, or can be prepared as a contiguous protein using genetic engineering techniques.

In a first preferred embodiment, the method of the invention comprises the step of mutating the human CH1γ1 domain from said antibody, so as to restore the pairing between CH1 and CL domains that is typical of other IgG subclasses.

CH1 domain from a human IgG1 is well known from the skilled person. As an example, the CH1 domain from a human IgG1 corresponds to SEQ ID NO:21.

As used herein, the step of "mutating the human CH1γ1 domain so as to restore the pairing between CH1 and CL domains that is typical of the other IgG subclasses", refers to a human CH1γ1 domain wherein an amino acid has been substituted by a cysteine residue, preferably wherein the amino acid in position 133 or 134 is a cysteine, and still preferably wherein the amino acid in position 133 is a cysteine. The numbering of the constant region is that of the EU index as set forth in Kabat et al. (1991, NIH Publication n° 91-3242, National technical Information Service Springfield, Va.). As a first example, such human CH1γ1 domain refers to the amino acid sequence SEQ ID NO: 1, wherein the serine residue in position 133 has been substituted by a cysteine. As a second example, such human CH1γ1 domain refers to the amino acid sequence SEQ ID NO: 22, wherein the serine residue in position 134 has been substituted by a cysteine. The cysteine residue at the 133 or 134 position of the CH1 sequence restores a disulfide bound between the light chain and the heavy chain of the antibodies of the invention. Table 1 provides sequences of CH1γ1 domains.

TABLE 1

| SEQ ID NO: 21 | ASTKGPSVFPLAPSSKSTSGGTAALGCLVKDYFPEPVTVSWNSGALTSGVHTFPAVLQSSGLYSLSSVVTVPSSSLGTQTYIC̲NVNHKPSNTKVDKKV |
| SEQ ID NO: 1 | ASTKGPSVFPLAPC̲SKSTSGGTAALGCLVKDYFPEPVTVSWNSGALTSGVHTFPAVLQSSGLYSLSSVVTVPSSSLGTQTYICNVNHKPSNTKVDKKV |
| SEQ ID NO: 22 | ASTKGPSVFPLAPSC̲KSTSGGTAALGCLVKDYFPEPVTVSWNSGALTSGVHTFPAVLQSSGLYSLSSVVTVPSSSLGTQTYIC̲NVNHKPSNTKVDKKV |

Advantageously, the step of mutating the human CH1γ1 domain from said antibody, so as to restore the pairing between CH1 and CL domains that is typical of other IgG subclasses, is done by:

a) isolating a nucleic acid sequence comprising the CH1 domain of a human immunoglobulin G class 1 (IgG1) antibody, said nucleic acid sequence preferably encoding the heavy chain of the antibody;

b) mutating a codon, preferably mutating the codon encoding position 133 or 134 of said CH1 domain to encode the amino acid residue cysteine (C) to provide a mutated nucleic acid sequence;

c) providing the mutated nucleic acid sequence with operable expression elements;

d) co-expressing the mutated nucleic acid with a nucleic acid sequence encoding the light chain of the antibody in a suitable host thereby providing a mutated human immunoglobulin G class 1 (IgG1) antibody, derivative or a functional fragment; and e) optionally, isolating the mutated antibody, derivative or fragment thereof.

In a second preferred embodiment, the method of the invention comprises the step of substituting said human CH1γ1 domain by the CH1 domain from a human IgG2 (CH1γ2), IgG3 (CH1γ3) or IgG4 (CH1γ4).

CH1 domain from a human IgG2, IgG3, and IgG4 are well known from the skilled person. As an example, CH1 domain from a human IgG2 corresponds to SEQ ID NO:23, the CH1 domain from a human IgG3 corresponds to SEQ ID NO:2, and the CH1 domain from a human IgG4 corresponds to SEQ ID NO:24. Table 2 provides sequences of CH1γ2, CH1γ3 and CH1γ4 domains.

TABLE 2

| SEQ ID NO: 23 | ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTV |
| SEQ ID NO: 2 | ASTKGPSVFPLAPCSRSTSGGTAALGCLVKDYFPEPVTVSWNSGALTSGVHTFPAVLQSSGLYSLSSVVTVPSSSLGTQTYTCNVNHKPSNTKVDKRV |
| SEQ ID NO: 24 | ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRV |

Advantageously, the step of substituting the human CH1γ1 domain from said antibody by the CH1 domain from a human IgG2 (CH1γ2), IgG3 (CH1γ3) or IgG4 (CH1γ4) is done by:

a) isolating a nucleic acid sequence comprising the CH1 domain of a human immunoglobulin G class 1 (IgG1) antibody, said nucleic acid sequence preferably encoding the heavy chain of the antibody;

b) substituting said CH1γ1 nucleic acid sequence by a nucleic acid sequence encoding the CH1 domain from a human IgG2 (CH1γ2), IgG3 (CH1γ3) or IgG4 (CH1γ4) to provide a mutated nucleic acid sequence;

c) providing the mutated nucleic acid sequence with operable expression elements;

d) co-expressing the mutated nucleic acid with a nucleic acid sequence encoding the light chain of the antibody in a suitable host thereby providing a mutated human immunoglobulin G class 1 (IgG1) antibody, derivative or a functional fragment; and e) optionally, isolating the mutated antibody, derivative or fragment thereof.

In a still preferred embodiment, the method of the invention further comprises the step of mutating the human hinge IgG1 domain from said antibody, so as to restore the pairing between the hinge and CH2 domains that is typical of other IgG subclasses, or of substituting said human hinge IgG1 domain by the hinge domain from a human IgG2, IgG3, IgG4, or a derivative thereof.

The hinge domain from a human IgG1 is well known from the skilled person and corresponds as an example to SEQ ID NO:3.

As used herein, the step of "mutating the human hinge domain from said antibody, so as to restore the pairing between hinge and CH2 domains that is typical of other IgG subclasses", refers to a human IgG1 hinge domain, wherein the cysteine residue at the fifth position of the hinge sequence has been substituted by another residue, preferably by a serine. In fact, said mutation results in the restoration of the typical IgG structure. As an example of such derivative, one can cite SEQ ID NO:4. Table 3 provides sequences of human IgG1 hinge domains.

TABLE 3

| SEQ ID NO: 3 | EPKSCDKTHTCPPCP |
| SEQ ID NO: 4 | EPKSSDKTHTCPPCP |

Advantageously, the step of mutating the human hinge domain from said antibody, so as to restore the pairing between hinge and CH2 that is typical of other IgG subclasses, is done by:

a) isolating a nucleic acid sequence comprising the hinge domain of a human immunoglobulin G class 1 (IgG1) antibody, said nucleic acid sequence preferably encoding the heavy chain of the antibody;

b) mutating the codon encoding the amino acid residue cysteine (C) at position 5 of said hinge domain to encode another amino acid residue, preferably a serine residue, to provide a mutated nucleic acid sequence;

c) providing the mutated nucleic acid sequence with operable expression elements;

d) co-expressing the mutated nucleic acid with a nucleic acid sequence encoding the light chain of the antibody in a suitable host thereby providing a mutated human immunoglobulin G class 1 (IgG1) antibody, derivative or a functional fragment; and e) optionally, isolating the mutated antibody, derivative or fragment thereof.

Hinge domain from a human IgG2, IgG3 or IgG4 are well known from the skilled person and corresponds as an example to SEQ ID NO:5 for IgG3. Derivatives of human IgG3 are also well known from the skilled person and correspond as an example to SEQ ID NO:6 to 9, preferably SEQ ID NO:9. Table 4 provides sequences of human IgG2, IgG3 or IgG4 hinge domains.

TABLE 4

| | |
|---|---|
| SEQ ID NO: 5 | ELKTPLGDTTHTCPRCPEPKSCDTPPPCPRCPEPKSCDTPPPC PRCPEPKSCDTPPPCPRCP |
| SEQ ID NO: 6 | ELKTPLGDTTHTCPRCPEPKSCDTPPPCPRCPEPKSCDTPPPC PRCP |
| SEQ ID NO: 7 | ELKTPLGDTTHTCPRCPEPKSCDTPPPCPRCP |
| SEQ ID NO: 8 | EPKSCDTPPPCPRCP |
| SEQ ID NO: 9 | ELKTPLGDTTHTCPRCP |

Still advantageously, the step of substituting the human hinge IgG1 domain from said antibody, by the hinge domain from a human IgG2, IgG3, IgG4, or a derivative thereof, is done by:

a) isolating a nucleic acid sequence comprising the hinge domain of a human immunoglobulin G class 1 (IgG1) antibody, said nucleic acid sequence preferably encoding the heavy chain of the antibody;

b) substituting said IgG1 hinge domain nucleic acid sequence by a nucleic acid sequence encoding the hinge domain from a human IgG2, IgG3, IgG4 or a derivative to provide a mutated nucleic acid sequence;

c) providing the mutated nucleic acid sequence with operable expression elements;

d) co-expressing the mutated nucleic acid with a nucleic acid sequence encoding the light chain of the antibody in a suitable host thereby providing a mutated human immunoglobulin G class 1 (IgG1) antibody, derivative or a functional fragment; and e) optionally, isolating the mutated antibody, derivative or fragment thereof.

In a second aspect, the present invention relates to an antibody, or functional fragment thereof, which can be obtained by the method of the invention, wherein said antibody comprises:

a) a light chain comprising the following amino acid sequences:

i) the Light Chain Variable Region (LCVR) specific from an antigen; and ii) a human kappa (κ) Constant (CL) domain; and b) a heavy chain comprising the following amino acid sequences:

i) the Heavy Chain Variable Region (HCVR) specific from said antigen;

ii) the CH2 and CH3 domains from a human IgG1; and iii) the CH1 domain from a human IgG1, which is mutated so as to restore the pairing between CH1 and CL domains that is typical of other IgG subclasses, or substituted by a CH1 domain from a human IgG2, IgG3 or IgG4.

The term "antibody", as used herein, refers to a monoclonal antibody per se. A monoclonal antibody can be a human antibody, chimeric antibody and/or humanized antibody.

Human kappa (κ) CL domain is well known from the skilled person and corresponds, as an example, to SEQ ID NO:10.

SEQ ID NO: 10    RTVAAPSVFIFPPSDEQLKSGTASVVCLLNNFYPREAKVQWKV

DNALQSGNSQESVTEQDSKDSTYSLSSTLTLSKADYEKHKVYA

CEVTHQGLSSPVTKSFNRGEC

CH2 and CH3 domains from a human IgG1 are well known from the skilled person and correspond as an example to SEQ ID NO: 11.

SEQ ID NO: 11    APELLGGPSVFLFPPKPKDTLMISRTPEVTCVVVDVSHEDPE

VKFNWYVDGVEVHNAKTKPREEQYNSTYRVVSVLTVLHQDWL

NGKEYKCKVSNKALPAPIEKTISKAKGQPREPQVYTLPPSRE

EMTKNQVSLTCLVKGFYPSDIAVEWESNGQPENNYKTTPPVL

DSDGSFFLYSKLTVDKSRWQQGNVFSCSVMHEALHNHYTQKS

LSLSPGK

The antibodies useful in the invention are produced recombinantly, as manipulation of the typically murine or other non-human antibodies with the appropriate specificity is required in order to convert them to humanized form. Antibodies may or may not be glycosylated, though glycosylated antibodies are preferred. Antibodies are properly cross-linked via disulfide bonds, as is well-known.

According to a preferred embodiment, the antibody of the invention is a chimeric antibody. By, the expression "chimeric antibody" is meant an antibody that is composed of variables regions from a murine immunoglobulin and of constant regions of a human immunoglobulin. This alteration consists simply of substituting the constant region of a human antibody for the murine constant region, thus resulting in a human/murine chimera which may have sufficiently low immunogenicity to be acceptable for pharmaceutical use. For the present invention, said chimeric antibody comprises the constant regions from human light and heavy chains. A number of methods for producing such chimeric antibodies have yet been reported, thus forming part of the general knowledge of the skilled artisan (See, e.g., U.S. Pat. No. 5,225,539).

According to another preferred embodiment, the antibody of the invention is a humanized antibody.

By "humanized antibody" is meant an antibody that is composed partially or fully of amino acid sequences derived from a human antibody germline by altering the sequence of an antibody having non-human complementarity determining regions (CDR). This humanization of the variable region of the antibody and eventually the CDR is made by techniques that are by now well known in the art.

As an example, British Patent Application GB 2188638A and U.S. Pat. No. 5,585,089 disclose processes wherein recombinant antibodies are produced where the only portion of the antibody that is substituted is the complementarity determining region, or "CDR". The CDR grafting technique has been used to generate antibodies which consist of murine CDRs, and human variable region framework and constant regions (See. e. g., RIECHMANN et al., Nature, vol. 332, p: 323-327, 1988). These antibodies retain the human constant regions that are necessary for Fc dependent effector function, but are much less likely to evoke an immune response against the antibody.

As an example, the framework regions of the variable regions are substituted by the corresponding human framework regions leaving the non-human CDR substantially intact, or even replacing the CDR with sequences derived from a human genome. Fully human antibodies are produced in genetically modified mice whose immune systems have been altered to correspond to human immune systems. As mentioned above, it is sufficient for use in the methods of the invention, to employ an immunologically specific fragment of the antibody, including fragments representing single chain forms.

A humanized antibody again refers to an antibody comprising a human framework, at least one CDR from a non-human antibody, and in which any constant region present is substantially identical to a human immunoglobulin constant region, i. e., at least about 85 or 90%, preferably at least 95% identical. Hence, all parts of a humanized antibody, except possibly the CDRs, are substantially identical to corresponding parts of one or more native human immunoglobulin sequences. For example, a humanized immunoglobulin would typically not encompass a chimeric mouse variable region/human constant region antibody.

Humanized antibodies have at least three potential advantages over non-human and chimeric antibodies for use in human therapy:

1) Because the effector portion is human, it may interact better with the other parts of the human immune system (e.g., destroy the target cells more efficiently by complement-dependent cytotoxicity (CDC) or antibody-dependent cellular cytotoxicity (ADCC)).

2) The human immune system should not recognize the framework or C region of the humanized antibody as foreign, and therefore the antibody response against such an injected antibody should be less than against a totally foreign non-human antibody or a partially foreign chimeric antibody.

3) Injected non-human antibodies have been reported to have a half-life in the human circulation much shorter than the half-life of human antibodies. Injected humanized antibodies will have a half-life essentially identical to naturally occurring human antibodies, allowing smaller and less frequent doses to be given.

As an example, the design of humanized immunoglobulins may be carried out as follows: When an amino acid falls under the following category, the framework amino acid of a human immunoglobulin to be used (acceptor immunoglobulin) is replaced by a framework amino acid from a CDR-providing non-human immunoglobulin (donor immunoglobulin): (a) the amino acid in the human framework region of the acceptor immunoglobulin is unusual for human immunoglobulin at that position, whereas the corresponding amino acid in the donor immunoglobulin is typical for human immunoglobulin at that position; (b) the position of the amino acid is immediately adjacent to one of the CDRs; or (c) any side chain atom of a framework amino acid is within about 5-6 angstroms (center-to-center) of any atom of a CDR amino acid in a three dimensional immunoglobulin model (QUEEN et al., Proc. Natl. Acad. Sci. USA, vol. 88, p: 2869, 1991). When each of the amino acid in the human framework region of the acceptor immunoglobulin and a corresponding amino acid in the donor immunoglobulin is unusual for human immunoglobulin at that position, such an amino acid is replaced by an amino acid typical for human immunoglobulin at that position.

According to another preferred embodiment, said antibody or fragment thereof is directed against an immunoregulator, an infectious or a tumoral antigen.

Light and Heavy Chain Variable Region (LCVR and HCVR) specific from such an antigen can be simply identified by the skilled person in view of its general knowledge.

As used herein, an "immunoregulator antigen" refers to an antigen expressed by either activated inducer immune cells, such as T and/or NK cells or by activated suppressor cells.

As an example of an antigen expressed by activated suppressor cells, one can cite CTL-A4 (Cytotoxic Lymphocyte Associated Antigen, also designated CD 152) was discovered in 1987 (BRUNET et al., Nature, vol. 328, p: 267-270, 1987).

As an example of antigen expressed by activated inducer immune cells, one can cite BTLA (B- and T-lymphocyte attenuator), also known as CD272, which is induced during activation of T cells, and remains expressed on Th1 cells but not Th2 cells.

As used herein an "infectious antigen" refers to an antigenic substance produced in cells infected by a microbe such as a bacteria or a virus.

As used herein a "tumoral antigen" refers to an antigenic substance produced in tumor cells. Many tumoral antigen are well known from the skilled person and one can cite, as non limiting examples, CD20, CEA, EGFR, HER2, EPCAM, MUC1, PSMA, CD-19, GM1, CAIX, phospholipid antigens such as phopshatidylserine or gangliosides such as GD2, GD2-O-acetylated or GD3.

Preferably, said antigen does not correspond to GD2-O-acetylated.

CD-20 is a non-glycosylated phosphoprotein expressed during early pre-B cell development and remains until plasma cell differentiation. Specifically, the CD20 molecule may regulate a step in the activation process which is required for cell cycle initiation and differentiation and is usually expressed at very high levels on neoplastic ("tumor") B cells. CD20, by definition, is present on both "normal" B cells as well as "malignant" B cells. Thus, the CD20 surface antigen has the potential of serving as a candidate for "targeting" of B cell lymphomas.

Concerning the antibodies directed against CD20, so as to obtain their corresponding Light and Heavy Chain Variable Regions (LCVR and HCVR) specific from CD20, one can cite rituximab ("RITUXAN®") (U.S. Pat. No. 5,736,137); the yttrium-[90]-labeled 2B8 murine antibody designated "Y2B8" or "Ibritumomab Tiuxetan" ZEVALIN® (U.S. Pat. No. 5,736,137); murine IgG2a "BI," also called "Tositumomab," optionally labeled with $^{131}$I to generate the "$^{131}$I-BI" antibody (iodide 131 tositumomab, BEXXAR®) (U.S. Pat. No. 5,595,721); and humanized 2H7; Ofatumumab, a fully humanized IgG1 against a novel epitope on CD20 huMax-CD20 (International patent application PCT WO 2004/035607). Among them, rituximab, ibritumomab, tiuxetan, and tositumomab received market approval for the treatment of specific lymphoma, and Ofatumumab received market approval for the treatment of specific leukemia. Preferably, said antibody directed against CD20 is rituximab and corresponds the sequences presented in the following table 5 for Heavy Chain Variable Regions (HCVR; SEQ ID NO: 25 to 31), and table 6 for Light Chain Variable Regions (LCVR; SEQ ID NO:32 to 37).

Anti-CD20 (Rituximab) Variable Heavy Chain:

TABLE 5

| | | |
|---|---|---|
| SEQ ID NO: 25 | FR1 | QVQLQQPGAELVKPGASVKMSCKAS |
| SEQ ID NO: 26 | CDR1 | GYTFTSYN |
| SEQ ID NO: 27 | FR2 | MHWVKQTPGRGLEWIGA |
| SEQ ID NO: 28 | CDR2 | IYPGNGDT |
| SEQ ID NO: 29 | FR3 | SYNQKFKGKATLTADKSSSTAYM QLSSLTSEDSAVYYC |
| SEQ ID NO: 30 | CDR3 | ARSTYYGGDWYFNV |
| SEQ ID NO: 31 | FR4 | WGAGTTVTVSA |

Anti-CD20 (Rituximab) Variable Light Chain (k Chain):

TABLE 6

| | | |
|---|---|---|
| SEQ ID NO: 32 | FR1 | QIVLSQSPAILSASPGEKVTMTCRAS |
| SEQ ID NO: 33 | CDR1 | SSVSY |
| SEQ ID NO: 34 | FR2 | IHWFQQKPGSSPKPWIY |
| | CDR2 | ATS |
| SEQ ID NO: 35 | FR3 | NLASGVPVRFSGSGSGTSYSLTI SRVEAEDAATYYC |
| SEQ ID NO: 36 | CDR3 | QQWTSNPPT |
| SEQ ID NO: 37 | FR4 | FGGGTKLEIK |

Still preferably, the CH1 and hinge sequence of rituximab corresponds to SEQ ID NO:38.

SEQ ID NO: 38   ASTKGPSVFPLAPSSKSTSGGTAALGCLVKDYFPEPVTVSWNS
                GALTSGVHTFPAVLQSSGLYSLSSVVTVPSSSLGTQTYICNVN
                HKPSNTKVDKKVEPKSCDKTHTCPPCP

The CEA (carcinoembryonic antigen) glycoprotein is a tumor marker involved in cell adhesion. Concerning the antibodies directed against CEA, so as to obtain their corresponding Light and Heavy Chain Variable Regions (LCVR and HCVR) specific from CEA, one can cite arcitumomab (IMMUNOMEDICS).

The ErbB receptors are expressed in various tissues of epithelial, mesenchymal and neuronal origin. Under normal conditions, activation of the ErbB receptors is controlled by the spatial and temporal expression of their ligands, which are members of the EGF family of growth factors. Ligand binding to ErbB receptors induces the formation of receptor homo- and heterodimers and activation of the intrinsic kinase domain, resulting in phosphorylation on specific tyrosine kinase residues within the cytoplasmic tail. These phosphorylated residues serve as docking sites for various proteins, the recruitment of which leads to the activation of intracellular signaling pathways. Among ErbB receptors, EGFR and HER2 are known to play an essential role in regulating cell proliferation and differentiation. They have a strong tendency to assemble with other HER receptors into homo- and/or heterodimers upon extracellular growth factor binding, which results in various forms of signal transduction pathways activation, leading to apoptosis, survival, or cell proliferation.

Concerning the antibodies directed against EGFR, so as to obtain their corresponding Light and Heavy Chain Variable Regions (LCVR and HCVR) specific from EGFR, one can cite the humanized monoclonal antibody 425, also designated as matuzumab (hMAb 425, U.S. Pat. No. 5,558,864; EP 0531 472), the chimeric monoclonal antibody 225 (cMAb 225), also designated as cetuximab (ERBITUX®; U.S. Pat. No. 7,060,808), and the fully human anti-EGFR antibody panitumumab (VECTIBIX®; U.S. Pat. No. 6,235, 883). Among them, cetuximab and panitumumab were demonstrated to inhibit human colorectal tumors in vivo and both received marked approval.

Concerning the antibodies directed against Her2, so as to obtain their corresponding Light and Heavy Chain Variable Regions (LCVR and HCVR) specific from Her2, one can cite the recombinant humanized version of the mouse antibody 4D5 ((U.S. Pat. No. 5,677,171), designated as huMAb4D5-8, rhuMAb HER2, trastuzumab, or HERCEPTIN® (U.S. Pat. No. 5,821,337). This antibody received marketing approval in 1998 for the treatment of patients with metastatic breast cancer whose tumors overexpress the ErbB2 protein. Preferably, said antibody directed against Her2 is trastuzumab and corresponds respectively to the sequences presented in the following table 7 for Heavy Chain Variable Regions (HCVR; SEQ ID NO: 39 to 45), and table 8 for Light Chain Variable Regions (LCVR; SEQ ID NO:46 to 51).

Anti-Her2 (Trastuzumab) Variable Heavy Chain:

TABLE 7

| | | |
|---|---|---|
| SEQ ID NO: 39 | FR1 | EVQLVESGGGLVQPGGSLRLSCAAS |
| SEQ ID NO: 40 | CDR1 | GFNIKDTY |
| SEQ ID NO: 41 | FR2 | IHWVRQAPGKGLEWVAR |
| SEQ ID NO: 42 | CDR2 | IYPTNGYT |
| SEQ ID NO: 43 | FR3 | RYADSVKGRFTISADTSKNTAYL QMNSLRAEDTAVYYC |
| SEQ ID NO: 44 | CDR3 | SRWGGDGFYAMDY |
| SEQ ID NO: 45 | FR4 | WGQGTLVTVSS |

Anti-Her2 (Trastuzumab) Variable Light Chain (k Chain):

TABLE 8

| SEQ ID NO: 46 | FR1 | DIQMTQSPSSLSASVGDRVTITCRAS |
| --- | --- | --- |
| SEQ ID NO: 47 | CDR1 | QDVNTA |
| SEQ ID NO: 48 | FR2 | VAWYQQKPGKAPKLLIY |
| | CDR2 | SAS |
| SEQ ID NO: 49 | FR3 | FLYSGVPSRFSGSRSGTDFTLTIS SLQPEDFATYYC |
| SEQ ID NO: 50 | CDR3 | QQHYTTPPT |
| SEQ ID NO: 51 | FR4 | FGQGTKVEIK |

Still preferably, the CH1 and hinge sequence of trastuzumab corresponds to SEQ ID NO:38.

GD2 is a disialoganglioside expressed on tumors of neuroectoderma origin, including neuroblastoma and melanoma. Concerning the antibodies directed against GD2, so as to obtain their corresponding Light and Heavy Chain Variable Regions (LCVR and HCVR) specific from GD2, one can cite the murine IgG3 monoclonal antibodies 3F8 and 14.18, or the chimeric monoclonal anti-GD2 antibody ch14.18 (made up of the variable region of the murine anti-GD2 antibody 14.18 and the constant region of human IgG1), which have been used in the treatment of neuroblastoma, or the murine IgG3 monoclonal antibody 8B6, which is specific of the O-acetylated form of GD2 (International patent application PCT WO 2008/043777). Preferably, said antibody directed against GD2 is ch14.18 and corresponds respectively to the sequences presented in the following table 9 for Heavy Chain Variable Regions (HCVR; SEQ ID NO: 52 to 57), and table 10 for Light Chain Variable Regions (LCVR; SEQ ID NO:58 to 63).

Anti-GD2 (ch14.18) Variable Heavy Chain:

TABLE 9

| SEQ ID NO: 52 | FR1 | EVQLLQSGPELEKPGASVMISCKAS |
| --- | --- | --- |
| SEQ ID NO: 53 | CDR1 | GSSFTGYN |
| SEQ ID NO: 54 | FR2 | MNWVRQNIGKSLEWIGA |
| SEQ ID NO: 55 | CDR2 | IDPYYGGT |
| SEQ ID NO: 56 | FR3 | SYNQKFKGRATLTVDKSSSTAYMELKSLT SEDSAVYYC |
| SEQ ID NO: 57 | CDR3 | VSGMEY |
| SEQ ID NO: 58 | FR4 | WGQGTSVTVSS |

Anti-GD2 (ch14.18) Variable Light Chain (k Chain):

TABLE 10

| SEQ ID NO: 59 | FR1 | DVVMTQTPLSLPISLGDQASISCRSS |
| --- | --- | --- |
| SEQ ID NO: 60 | CDR1 | QSLVHRNGNTYL |
| SEQ ID NO: 61 | FR2 | HWYLQKPGQSPKLLIH |
| | CDR2 | KVS |
| SEQ ID NO: 62 | FR3 | NRFSGVPDRFSGSGSGTDFTLKI SRVEAEDLGVYFC |
| SEQ ID NO: 63 | CDR3 | SQSTHVPPLT |
| SEQ ID NO: 64 | FR4 | FGAGTKLELN |

Still preferably, the CH1 and hinge sequence of ch14.18 corresponds to SEQ ID NO:38.

As used herein, a "tumoral antigen" may also refer to a tumor neovascularization or to a tumor extracellular matrix antigen.

As used herein, an "antigen related to tumor neovascularization" refers to an antigen which is expressed by the neo-synthetized blood vessels present in the tumor.

As an example of such antigen, one can cite the EDA and the EDB domains of fibronectin, Endosalin/TEM1, Endoglin/105, PSMA or B7-H4.

As used herein, an "antigen related to tumor extracellular matrix" refers to an antigen which is expressed in the extracellular matrix present in the tumor.

As an example of such antigen, one can cite the G45 fragment of laminin-332 (ROUSSELLE et al., *Cancer Research*, vol. 68(8), p: 2885-94, 2008).

According to another preferred embodiment, the antibody of the invention comprises a human CH1γ1 domain wherein an amino acid has been substituted by a cysteine residue, preferably wherein the amino acid in position 133 or 134 is a cysteine, and still preferably wherein the amino acid in position 133 is a cysteine. The numbering of the constant region is that of the EU index as set forth in Kabat et al. (1991, NIH Publication n° 91-3242, National technical Information Service Springfield, Va.). As an example, such mutated human CH1γ1 domain refers to the amino acid sequence SEQ ID NO: 1, wherein the serine residue in position 133 has been substituted by a cysteine. The cysteine residue at the 133 or 134 position of the CH1 sequence restores a disulfide bound between the light chain and the heavy chain of the antibodies of the invention.

According to still another preferred embodiment, the antibody of the invention comprises a CH1 domain from a human IgG2, IgG3 or IgG4, preferably said domain is a CH1 domain from an IgG3, such as the sequence SEQ ID NO:2.

Whereas the antibody of the invention may comprise a hinge domain from a human IgG1, it may also comprise a human hinge domain, which is a human hinge IgG1 mutated so as to restore the typical IgG pairing, or which is a hinge domain from a human IgG2, IgG3, IgG4, or a derivative thereof.

A "human hinge IgG1 mutated so as to restore the typical IgG pairing", refers to a IgG1 hinge domain, wherein the cysteine residue at the fifth position of its sequence has been substituted by another residue, preferably by a serine. In fact, said mutation results in the restoration of the typical IgG structure. As an example of such derivative, one can cite SEQ ID NO:4.

Hinge domain from a human IgG2, IgG3 or IgG4 are well known from the skilled person and corresponds as an example to SEQ ID NO:5 for IgG3. Derivatives of human IgG3 are also well known from the skilled person and correspond as an example to SEQ ID NO:6 to 9, preferably SEQ ID NO:9.

Preferably, the introduction of a cysteine residue within the antibodies of the invention either by a mutated CH1 domain from a human IgG1 presenting a cysteine residue at the 133 or 134 positions of its sequence, or by a CH1 domain from a human IgG2, IgG3 or IgG4 do not liberate any free thiol group previously linked to another cysteine residue.

The antibodies of the invention encompass immunoconjugates.

As used herein, the term "immunoconjugate" refers to a conjugate molecule comprising at least one chimeric antibody or a functional fragment thereof, bound to a second molecule, preferably a cytotoxic agent or a radioisotope. Preferably, said antibody or functional fragment thereof is bound to said second molecule by covalent linkage.

In one embodiment, the antibody of the invention is an immunoconjugate.

In a particular embodiment, the antibody of the invention is an immunoconjugate wherein said immunoconjugate comprises an antibody of the invention or a functional fragment thereof and a cytotoxic agent.

In another particular embodiment, the antibody of the invention is an immunoconjugate wherein said immunoconjugate comprises an antibody of the invention or a functional fragment thereof and a radioisotope.

According to a third aspect, the present invention is related to a composition, preferably a pharmaceutical composition, comprising at least one antibody as described herein, or at least one functional fragment thereof and a pharmaceutically acceptable carrier for use in therapy.

Said composition is particularly useful for treating cancer, autoimmune disease or infection.

Said composition may be in any pharmaceutical form suitable for administration to a patient, including but not limited to solutions, suspensions, lyophilized powders, capsule and tablets.

The pharmaceutical compositions of the invention may further comprise any pharmaceutically acceptable diluent, excipient or auxiliary.

The pharmaceutical composition of the invention may be formulated for injection, e.g. local injection, transmucosal administration, inhalation, oral administration and more generally any formulation that the skilled person finds appropriate to achieve the desired therapy.

The antibody of the invention is contained in said pharmaceutical composition in an amount effective to achieve the intended purpose, and in dosages suitable for the chosen route of administration.

More specifically, a therapeutically effective dose means an amount of a compound effective to prevent, alleviate or ameliorate symptoms of the subject suffering from cancer or from an infection.

Depending on the intended application, the chimeric antibody of the invention may further comprise additional constituents. As an example, the chimeric antibody of the invention may correspond to an immunoconjugate.

A forth aspect of the present invention concerns a method for treating cancer or an infection comprising the step of administrating to a patient in need thereof an effective amount of the composition as described herein, which comprises at least one antibody, or at least one functional fragment thereof as described herein.

As used herein, the term "patient" refers to a mammal, preferably to a human.

Other embodiments and advantages of the present invention are illustrated in the following non-limiting examples.

EXAMPLES

1—Pro-Apoptotic Activity of Anti-OAcGD2 Antibody In Vitro

In a first step, the chimeric anti-OAcGD2 antibody, c8B6, has been designed from 8B6 by substituting its constant regions by the one of a human IgG1,κ. Its sequences are represented in FIG. 1 (SEQ ID NO: 12 and SEQ ID NO: 13).

The structure of this antibody comprises 2 intramolecular disulfide bonds in light chain (Cys23-Cys93 and Cys139-Cys199), and 4 intramolecular disulfide bonds in heavy chain (Cys22-Cys98, Cys146-Cys202, Cys263-Cys323, and Cys369-Cys427). Cysteine residues involved in intra-chain disulfide bonds are indicated by a star (*). The whole structure is stabilized by 3 intermolecular disulfide bonds: light chain is connected to heavy chain by one disulfide bond between the last cysteine residue of light chain and the cysteine residue of the upper hinge region (Cys219-Cys 222), and heavy chains are connected by 2 disulfide bonds connecting the Cysteine in the middle hinge (Cys228-Cys228 and Cys231-Cys231). Cysteine residues involved in inter-chain disulfide bonds are indicated by a arrow (I).

The 8B6 LCVR is cloned NotI-KasI in a pEvi vector so as to be fused with the CL domain of a human IgG1.

The 8B6 HCVR domain is cloned NotI-NheI in a pEvi' vector so as to be fused with the constant domain of the heavy chain of a human IgG1.

Then, CHO K1 cells are co-transfected by both vectors.

After transfection, the CHO K1 cells are maintained in a serum free medium for several days.

Each day, the culture medium is harvested and freezed at −80° C. A new medium is added to the transfected cells until the cell viability is less than 70-80%.

The harvested culture media are pooled and the antibody is purified using protein A immobilized on a sepharose matrix.

The production of c8B6 in CHO was analyzed by electrophoresis under both reducing and non-reducing conditions. The results have shown that under non-reducing conditions, the c8B6 antibody showed one band at 150 kD corresponding to whole antibody. While, under reducing conditions, a band at 50 kD for HC and a band at 25 kD for LC were observed. The gel filtration on a SUPERDEX Column showed a chromatogram profile with a main peak (99.0% for the degree purity) at 12.3 ml corresponding to 150 kD. Finally, the yield of production for the chimeric c8B6 after purification on a protein A column was about 315 mg/L of supernatant.

The binding of the antibody to its target was confirmed by flow cytometry on IRM5 cells expressing GD2-O-Acetylated ganglioside. The binding was revealed by a goat anti-human IgG conjugated to fluorescein isothiocyanate (FITC). These experiments have confirmed the functionality of this antibody, which binds GD2-O-Acetylated.

Then, the direct cytotoxicity of c8B6 antibody was evaluated by MTT assays.

In these assays, $1 \times 10^4$ IMR5 cells are incubated 24h at 37° C. in a 96-well microplate. Antibodies from 80-0.15 μg/mL were added and incubated 24h at 37° C. Fifty μg of MTT were then added to each well and incubated at least 4h at 37° C., before cells were solubilized with 10% SDS and to incubate O.N. at 37° C. The absorbance was then read at 570 and 650 nm. Absorbance of the product at 650 nm was subtracted from the absorbance at 570 nm (Abs570-Abs650) to calculate total conversion of dye. Four control wells with cells treated with 20 µg etoposide provide the blank for absorbance giving the 0% of viability. The inhibition of viability (%) was expressed as a percentage relative to the untreated cells and each value is represented as mean±SEM in quadruplicate.

The results have shown that the antibody c8B6 has lost the direct cytotoxicity of 8B6 following the chimerization step by passing from murine constant IgG3 domains to human IgG1 constant domains. Moreover, the antibody further lost the cooperativity properties of the parental IgG3 8B6.

Finally, many experiments trying different ways of chimerization only restore little pro-apoptotic activity, and no cooperativity in the binding was observed.

Surprisingly, specific modifications of the CH1 constant domain for the chimerization results in great changes for the pro-apoptotic activity.

These results were obtained with the antibodies 301.14a, 301.14b, 301.15, 301.15b, 301.16, 301.17, 301.18, 301.19, 301.20 and 301.21 which were designed on the basis of the previous constructions.

The antibody 301.14a corresponds to a mutated human CH1γ1 (underlined mutation S133C) with the human Hingeγ1 domain as represented in FIG. 2 (SEQ ID NO: 14). The other constant domains correspond to CH2 and CH3 domains of IgG1 (SEQ ID NO: 11) and the kappa CL domain (SEQ ID NO: 10).

The antibody 301.14b corresponds to a mutated human CH1γ1 (underlined mutation S133C) with a mutated human Hingeγ1 domain (underlined mutation C222S) as represented in FIG. 3 (SEQ ID NO:15). The other constant domains corresponds to CH2 and CH3 domains of IgG1 (SEQ ID NO: 11) and the kappa CL domain (SEQ ID NO: 10).

The antibody 301.15 corresponds to a human CH1γ3 (replacing its cousin CH1γ1) with the human Hingeγ1 domain as represented in FIG. 4 (SEQ ID NO:16). The other constant domains correspond to CH2 and CH3 domains of IgG1 (SEQ ID NO: 11) and the kappa CL domain (SEQ ID NO:10).

The antibody 301.15b corresponds to a human CH1γ3 (replacing its cousin CH1γ1) with a mutated human Hingeγ1 domain (underlined mutation corresponding to the substitution of the cysteine 222 by a serine residue, C222S) as represented in FIG. 9 (SEQ ID NO:66). The other constant domains correspond to CH2 and CH3 domains of IgG1 (SEQ ID NO:9) and the kappa CL domain (SEQ ID NO:8).

The antibody 301.16 corresponds to a mutated human CH1γ1 (underlined mutation S133C) with the human Hingeγ3 domain (replacing its cousin Hingeγ1) as represented in FIG. 5 (SEQ ID NO: 17). The other constant domains correspond to CH2 and CH3 domains of IgG1 (SEQ ID NO: 11) and the kappa CL domain (SEQ ID NO: 10).

The antibody 301.17 corresponds to a human CH1γ3 (replacing its cousin CH1γ1) with the human Hingeγ3 domain (replacing its cousin Hingeγ1) as represented in FIG. 6 (SEQ ID NO:18). The other constant domains correspond to CH2 and CH3 domains of IgG1 (SEQ ID NO: 11) and the kappa CL domain (SEQ ID NO: 10).

The antibody 301.18 corresponds to a mutated human CH1γ1 (underlined mutation S133C) with a shortened (17 amino acids) human Hingeγ3 domain as represented in FIG. 7 (SEQ ID NO:19). The other constant domains correspond to CH2 and CH3 domains of IgG1 (SEQ ID NO: 11) and the kappa CL domain (SEQ ID NO: 10).

The antibody 301.19 corresponds to a human CH1γ3 (replacing its cousin CH1γ1) with a shortened (17 amino acids) human Hingeγ3 domain as represented in FIG. 8 (SEQ ID NO:20). The other constant domains correspond to CH2 and CH3 domains of IgG1 (SEQ ID NO: 11) and the kappa CL domain (SEQ ID NO: 10).

The antibody 301.20 corresponds to a human CH1γ2 (replacing its cousin CH1γ1) with the human Hingeγ1 domain as represented in FIG. 10 (SEQ ID NO:23). The other constant domains correspond to CH2 and CH3 domains of IgG1 (SEQ ID NO:9) and the kappa CL domain (SEQ ID NO:8).

The antibody 301.21 corresponds to a human CH1γ4 (replacing its cousin CH1γ1) with the human Hingeγ1 domain as represented in FIG. 11 (SEQ ID NO:24). The other constant domains correspond to CH2 and CH3 domains of IgG1 (SEQ ID NO:9) and the kappa CL domain (SEQ ID NO:8).

The muIgG3 control corresponds to a murine 8B6 IgG3, wherein the CH1 IgG3 corresponds to SEQ ID NO:64, wherein the cysteine residue at position 134 is substituted by a serine residue and the serine residue at position 224 is substituted by a cysteine residue.

SEQ ID NO: 64   ATTTAPSVYPLVPGCSDTSGSSVTLGCLVKGYFPEPVTVKWNY
GALSSGVRTVSSVLQSGFYSLSSLVTVPSSTWPSQTVICNVAH
PASKTELIKRIEPRIPKPCTPPGSSCP

The binding of said antibodies to GD2-O-Acetylated ganglioside was confirmed as previously.

Then, the potential pro-apoptotic activities of said antibodies were determined as mentioned previously.

The results are summarized in the following tables, wherein the percentage of lysis is the one obtained for antibody concentration of 80 µg/ml.

Table 11 presents direct cytotoxicity of anti-OacGD2 301.14a, 301.14b, 301.15, 301.16, 301.17, 301.18 and 301.19 antibodies on IMR5 cells:

TABLE 11

| Construction | Mean +/− SEM of n = 2 experiments | | Affinity (Eq) |
| --- | --- | --- | --- |
| | $EC_{50}$ (µg/ml) | % Maximal lysis | Kd (nM) |
| 8B6 | 10.0 ± 1.8 | 33.3 ± 5.6 | 46.9 ± 15.0 |
| c8B6 | 14.7 ± 16.6 | 7.3 ± 5.4 | 208.3 ± 90.9 |
| 301.14a | 6.5 ± 0.3 | 20.2 ± 7.4 | ND |
| 301.14b (n = 1) | 1.0 | 33.8 | 103.6 ± 22.5 |
| 301.15 | 3.6 ± 2.0 | 45.0 ± 13.9 | 161.9 ± 42.0 |
| 301.16 | 2.1 ± 2.0 | 29.2 ± 17.3 | ND |
| 301.17 | 3.2 ± 0.8 | 20.8 ± 3.0 | ND |
| 301.18 | 8.5 ± 0.6 | 31.0 ± 1.7 | 63.9 ± 8.6 |
| 301.19 | 7.6 ± 1.4 | 37.5 ± 0.5 | 54.5 ± 6.2 |

The results show that unexpectedly, the chimeric antibodies comprising a mutated human CH1γ1 6 or a human CH1γ3 have a pro-apoptotic activity, meaning that loss of direct cytotoxicity might be due to the structure of human IgG1. Moreover, these antibodies all show an $EC_{50}$ greater than the one of the initial antibody 8B6.

The results have also shown that construction that gave the higher cytotoxic effect in terms of maximal % lysis correspond (i) to fusion of human CH1γ3 and human Hingeγ1 (301.15 construct) or (ii) to fusion of human CH1 γ1 (mutated on S133C) or human CH1 γ3 and shortened-Human Hinge γ3 (301.18 and 301.19 constructions). For these 2 latest, an increase of affinity in comparison to original c8B6 was observed.

Finally, and still surprisingly, the 301.15 antibody was the only one to present an aggregative profile in competition curves corresponding to a restored binding cooperativity.

Table 12 presents direct cytotoxicity of anti-OacGD2 301.15b, 301.20 and 301.21 antibodies on IMR5, SUM159PT and H187 cells:

TABLE 12

| Cell line | Antibody | Max lysis (80 µg/ml) | EC50 (µg/ml) |
|---|---|---|---|
| IMR5 | 301.15b | 58.67 | 2.53 |
| | 301.20 | 79.92 | 11.60 |
| | 301.21 | 60.88 | 26.12 |
| SUM159PT | 8B6 | 64.76 | 25.42 |
| | 301.14b | 63.99 | 1.92 |
| | 301.15 | 75.53 | 19.19 |
| | c8B6 | 0.00 | ND |
| H187 | 8B6 | 68.46 | 3.30 |
| | 301.14b | 65.42 | 2.27 |
| | 301.15 | 70.96 | 7.72 |
| | c8B6 | 0.00 | ND |

The results show that unexpectedly, the chimeric antibodies comprising a human CH1γ2 or CH1γ4 have a pro-apoptotic activity on IMR5 cells, meaning that loss of direct cytotoxicity might be due to the structure of human IgG1. Moreover, the chimeric antibodies comprising a human CH1γ3 and a mutated human Hingeγ1 domain (underlined mutation corresponding to the substitution of the cysteine 222 by a serine residue, C222S) have a pro-apoptotic activity on IMR5 cells.

The results have also shown that constructions corresponding to fusion of human CH1 γ1 (mutated on S133C) and a mutated human Hingeγ1 domain (underlined mutation corresponding to the substitution of the cysteine 222 by a serine residue, C222S) (301.14b construct) or to fusion of human CH1γ3 and human Hingeγ1 (301.15 construct) have pro-apoptotic activity on both SUM159PT and H187 cells.

Direct cytotoxicity of 301.14b and 301.15 antibodies was also assessed by propidium iodide assay.

In this assay, 150,000 IMR5 cells were plated in 24-well plates for 24h at 37° C. and then treated for 24h at 37° C. with 40 µg/mL of each antibodies. Thereafter, dead cells were labeling by propidium iodide (12.5 µg/ml). All samples were analyzed by flow cytometry in a LSRII FACS (BECTON DICKINSON).

The results are summarized in the following table 13 and illustrated by FIG. 12.

TABLE 13

| | % of dead cells | SEM |
|---|---|---|
| PBS | 20.2 | 1.00 |
| c8B6 (301.3) | 22.6 | 1.79 |
| 8B6 (301.4) | 67.7 | 1.90 |
| 301.14b | 46.8 | 2.61 |
| 301.15 | 48.0 | 0.77 |
| huIgG1 control | 20.2 | 0.98 |
| muIgG3 control | 22.4 | 1.59 |

The results confirmed that constructions corresponding to fusion of human CH1 γ1 (mutated on S133C) and a mutated human Hingeγ1 domain (underlined mutation corresponding to the substitution of the cysteine 222 by a serine residue, C222S) (301.14b construct) or to fusion of human CH1γ3 and human Hingeγ1 (301.15 construct) have pro-apoptotic activity on IMR5 cells. Simultaneously, the results confirm that a mutation in the murine IgG3 8B6 so as to mimic the IgG1 structure results in a loss of pro-apoptotic activity.

Reconstituting the pairing between the CH1 and the light chain, typical of non-IgG1 antibodies, could restore pro-apoptotic activity. Such reconstitution could be obtained by restoring the CH1 cysteine typical from non-IgG1 subclasses or by substituting a non-IgG1 CH1 domain.

In conclusion, the inventors succeed in the chimerization of the 8B6 antibody with a maintained pro-apoptotic activity, which pro-apoptotic activity is even increased for two antibodies, one of which showing also a cooperative binding like the original antibody.

2—Pro-Apoptotic Activity of Anti-GD2 Antibody In Vitro

The direct cytotoxicity of ch14.18 antibody was evaluated by MTT assays.

In this assays, $1 \times 10^4$ IMR5 cells (100 µl) were incubated in a 96-well microplate and incubated 24h at 37° C. Antibodies from 80 to 0.15 µg/mL in 50 µl medium were added and incubated 24h at 37° C. 50 µg of MTT were added and incubated 4h at 37° C., cells were solubilized and after night absorbance reading at 570 and 650 nm. Absorbance of the product at 650 nm was subtracted from the absorbance at 570 nm (Abs570-Abs650) to calculate total conversion of dye. Four control wells with cells treated with 20 µg etoposide provide the blank for absorbance giving the 0% of viability. The inhibition of viability (%) was expressed as a percentage relative to the untreated cells.

The results, obtained with 311.14b and 311.15 antibodies, are summarized in the following tables, wherein the percentage of lysis is the one obtained for antibody concentration of 80 µg/ml.

The antibody 311.14b corresponds to a mutated human CH1γ1 (underlined mutation S133C) with a mutated human Hingeγ1 domain (underlined mutation corresponding to the substitution of the cysteine 222 by a serine residue, C222S) as represented in FIG. 3 (SEQ ID NO:15). The other constant domains correspond to CH2 and CH3 domains of IgG1 (SEQ ID NO:9) and the kappa CL domain (SEQ ID NO:8).

The antibody 311.15 corresponds to a human CH1γ3 (replacing its cousin CH1γ1) with the human Hingeγ1 domain as represented in FIG. 4 (SEQ ID NO:16). The other constant domains correspond to CH2 and CH3 domains of IgG1 (SEQ ID NO:9) and the kappa CL domain (SEQ ID NO:8).

Table 14 presents direct cytotoxicity of anti-GD2 311.14b and 311.15 antibodies on IMR5 cells:

TABLE 14

| | | % max lysis (80 µg/ml) | EC$_{50}$ (µg/ml) |
|---|---|---|---|
| IMR5 | 14.18 (311.4) | 57.83 | 8.37 |
| | 311.14b | 68.71 | 9.14 |
| | 311.15 | 64.07 | 6.34 |
| | ch14.18 | 8.50 | ND |

The results show that unexpectedly, the chimeric antibodies comprising a mutated human CH1γ1 6 or a human CH1γ3 have a pro-apoptotic activity, meaning that loss of direct cytotoxicity might be due to the structure of human IgG1. Moreover, these antibodies all show an $EC_{50}$ similar to the one of the initial antibody 14.18.

Direct cytotoxicity of 311.14b and 311.15 antibodies was also assessed by propidium iodide assay.

In this assay, 150,000 IMR5 cells were plated in 24-well plates for 24h at 37° C. and then treated for 24h at 37° C. with 40 µg/mL of each antibodies. Thereafter, dead cells were labeling by propidium iodide (12.5 µg/ml). All samples were analyzed by flow cytometry in a LSRII FACS (Becton Dickinson, San Jose, Calif., USA).

Figure 13:
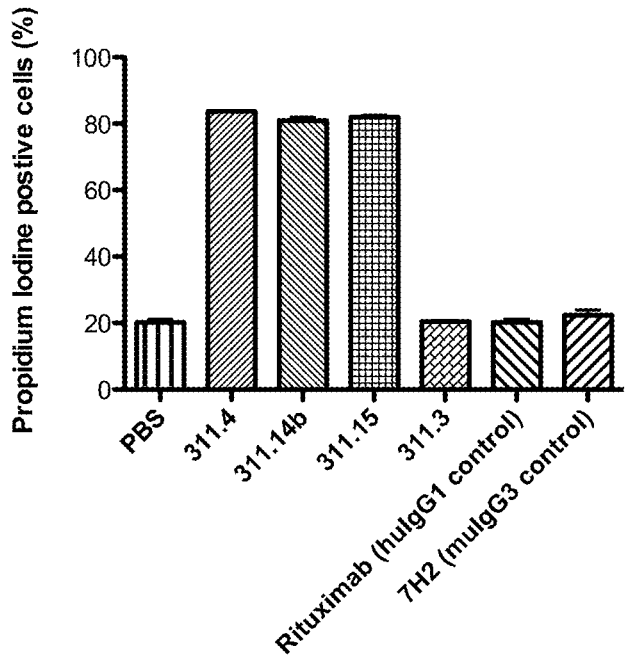
FIG. 13 shows the direct cytotoxicity of anti-GD2 antibodies by propidium iodide.

The results are summarized in the following table 15 and illustrated by FIG. 13.

TABLE 15

|  | % of dead cells | SEM |
| --- | --- | --- |
| PBS | 20.2 | 1.00 |
| ch14.18 (311.3) | 20.4 | 0.24 |
| 14.18 (311.4) | 83.8 | 0.19 |
| 311.14b | 80.8 | 1.13 |
| 311.15 | 80.7 | 0.65 |
| huIgG1 control | 20.2 | 0.98 |
| muIgG3 control | 22.4 | 1.59 |

The results confirmed that constructions corresponding to fusion of human CH1 γ1 (mutated on S133C) and a mutated human Hingeγ1 domain (underlined mutation corresponding to the substitution of the cysteine 222 by a serine residue, C222S) (311.14b construct) or to fusion of human CH1γ3 and human Hingeγ1 (311.15 construct) have pro-apoptotic activity on IMR5 cells.

Reconstituting the pairing between the CH1 and the light chain, typical of non-IgG1 antibodies, could restore pro-apoptotic activity. Such reconstitution could be obtained by restoring the CH1 cysteine typical from non-IgG1 subclasses or by substituting a non-IgG1 CH1 domain.

In conclusion, the inventors succeed in the chimerization of the 14.18 antibody with a maintained pro-apoptotic activity, which pro-apoptotic activity is even increased for two antibodies, one of which showing also a cooperative binding like the original antibody.

3—Anti-OAcGD2 Antibody Efficiency In Vivo
Murine Neuroblastoma Model
NOD/SCID mice, aged 5 weeks, were purchased from Charles River (L'Arbresle, France).

The human neuroblastoma IMR5 tumors were grown in immunodeficient NOD-SCID mice. Mice were injected subcutaneously with tumor cells ($1\times10^6$ IMR5 cells) on the right flank. Subcutaneous tumor growth was measured after tumor implantation using the formula [Volume $mm^3$= (length)×(width$^2$)×0.5]. In the IMR5 human neuroblastoma-bearing NOD/SCID mice, antibody (500 microg/mouse) was given i.v. when the tumor volume was equal to 0.1 $cm^3$.

Mice received 8B6 (muIgG3) mAb, or c.8B6 (huIgG1) mAb, or double mutated huIgG1 mAb, or huIgG1 CH1 substituted by huIgG3 CH1.

4—Anti-GD2 Antibody Efficiency In Vivo
Murine Neuroblastoma Model
NOD/SCID mice, aged 5 weeks, were purchased from CHARLES RIVER (L'Arbresle, France).

The human neuroblastoma IMR5 tumors were grown in immunodeficient NOD-SCID mice. Mice were injected subcutaneously with tumor cells ($1\times10^6$ IMR5 cells) on the right flank. Subcutaneous tumor growth was measured after tumor implantation using the formula [Volume $mm^3$= (length)×(width$^2$)×0.5]. In the IMR5 human neuroblastoma-bearing NOD/SCID mice, antibody (500 microg/mouse) was given i.v. when the tumor volume was equal to 0.1 $cm^3$.

Mice received 14.18 (muIgG3) mAb, or ch 14.18 (huIgG1) mAb, or double mutated huIgG1 mAb, or huIgG1 CH1 substituted by huIgG3 CH1.

5—Anti-CD20 Antibody Efficiency In Vivo
Murine Lymphoma Model
NOD/SCID mice, aged 5 weeks, were purchased from Charles River (L'Arbresle, France).

The human Burkitt's lymphoma Raji tumors were grown in immunodeficient NOD-SCID mice. Mice were injected subcutaneously with tumor cells ($1\times10^7$ Raji cells) on the right flank. Subcutaneous tumor growth was measured after tumor implantation using the formula [Volume $mm^3$= (length)×(width$^2$)×0.5]. In the Raji human lymphoma-bearing NOD/SCID mice, antibody (500 microg/mouse) was given i.v. when the tumor volume was equal to 0.1 $cm^3$.

Mice received rituximab chIgG1 mAb, or double mutated chIgG1 mAb, or chIgG1 mAb with the huIgG1 CH1 substituted by huIgG3 CH1.

6—Anti-HER2 (Trastuzumab) Antibody Efficiency In Vivo
Murine Breast Model
NOD/SCID mice, aged 5 weeks, were purchased from Charles River (L'Arbresle, France).

The human breast SKBR-3 tumors were grown in immunodeficient NOD-SCID mice. Mice were injected subcutaneously with tumor cells ($2\times10^6$ SKBR-3 cells) on the right flank. Subcutaneous tumor growth was measured after tumor implantation using the formula [Volume $mm^3$= (length)×(width$^2$)×0.5]. In the SKBR-3 human breast-bearing NOD/SCID mice, antibody (500 microg/mouse) was given i.v. when the tumor volume was equal to 0.1 $cm^3$.

Mice received trastuzumab humanised IgG1 mAb, or double mutated humanised IgG1 mAb, or humanised IgG1 mAb with the huIgG1 CH1 substituted by huIgG3 CH1.

We claim:

1. A method for increasing the antibody-directed pro-apoptotic activity of a human-mouse chimeric IgG1 monoclonal antibody for which the pairing pattern between the CH1 and CL domains was lost by chimerization, and as a result thereof the pro-apoptotic activity was lost, the human-mouse chimeric IgG1 monoclonal antibody being specific for a tumoral antigen produced by a tumor cell, or functional fragment thereof, comprising the steps of:
   A) restoring the disulfide pairing pattern between CH1 and CL domains similar to that existing in the human IgG2, IgG3 and IgG4 subclasses by substituting one amino acid at position 133 or 134 according to EU numbering of the human CH1γ1 domain of said antibody by a cysteine residue, or by substituting said human CH1γ1 domain with the CH1 domain of human IgG2 (CH1γ2), IgG3 (CH1γ3) or IgG4 (CH1γ4), wherein said modified human-mouse chimeric IgG1 monoclonal antibody comprises:
      a) a light chain comprising
         i) a Light Chain Variable Region (LCVR) specific for said tumoral antigen, and
         ii) a human kappa (K) Constant (CL) domain from a human IgG1 having the sequence SEQ ID NO:10; and
      b) a heavy chain comprising
         i) a Heavy Chain Variable Region (HCVR) specific for said tumoral antigen, and
         ii) CH2 and CH3 domains from a human IgG1 having the sequence SEQ ID NO: 11,
   B) contacting a tumor cell producing the tumoral antigen with the CH1γ1 modified human-mouse chimeric IgG1 monoclonal antibody obtained in step A),
      wherein the binding of the CH1γ1 modified human-mouse chimeric IgG1 monoclonal antibody to the tumor cell producing the tumoral antigen enhances tumor cell apoptosis,
      wherein the pro-apoptotic activity of the CH1γ1 modified human-mouse chimeric IgG1 monoclonal antibody toward tumor cell is increased as compared to that obtained with a non-modified human-mouse chimeric IgG1 monoclonal antibody having native CH1γ1 domain, of the same binding specificity under the same binding conditions, and
      wherein the cysteine residue introduced within the CH1 domain do not liberate any free thiol group previously bonded to another cysteine residue anywhere in the antibody molecule.

2. The method of claim 1, wherein the increased pro-apoptotic activity of the modified human-mouse chimeric IgG1 monoclonal antibody, or functional fragment thereof results in a higher degree of tumoral antigen bearing tumor cell-depletion as compared to that obtained with a non-modified human-mouse chimeric IgG1 monoclonal antibody having a native CH1γ1 domain, of the same binding specificity under the same binding conditions.

3. The method of claim 1, wherein the step of restoring the disulfide pairing pattern between CH1 and CL domains similar to that existing in human IgG2, IgG3 and IgG4 subclasses comprises substituting one amino acid at position 133 or 134 according to EU numbering of the human CH171 domain from said antibody by a cysteine residue.

4. The method of claim 3, wherein the step of restoring the disulfide pairing pattern between CH1 and CL domains similar to that existing in human IgG2, IgG3 and IgG4 subclasses by substituting one amino acid at position 133 or 134 according to EU numbering of the human CH1γ1 domain from said antibody by a cysteine residue comprises:
   a) isolating a nucleic acid sequence comprising the CH1 domain of a human-mouse chimeric IgG1 monoclonal antibody, said nucleic acid sequence preferably encoding the heavy chain of the antibody;
   b) mutating a codon encoding position 133 or 134 of said CH1 domain to encode the amino acid residue cysteine (C) to provide a mutated nucleic acid sequence;
   c) providing the mutated nucleic acid sequence with operable expression elements;
   d) co-expressing the mutated nucleic acid with a nucleic acid sequence encoding the light chain of the antibody in a suitable host thereby providing a mutated human-mouse chimeric IgG1 monoclonal antibody, or functional fragment thereof; and
   e) optionally, isolating the mutated antibody, or functional fragment thereof.

5. The method of claim 1, wherein the step of restoring the disulfide pairing pattern between CH1 and CL domains similar to that existing in human IgG2, IgG3 and IgG4 subclasses comprises substituting said human CH1γ1 domain with the CH1 domain of human IgG2 (CH1γ2), IgG3 (CH1γ3) or IgG4 (CH1γ4).

6. The method of claim 5, wherein the step of restoring the disulfide pairing pattern between CH1 and CL domains similar to that existing in human IgG2, IgG3 and IgG4 subclasses by substituting the human CH1γ1 domain from said antibody with the CH1 domain of human IgG2 (CH1γ2), IgG3 (CH1γ3) or IgG4 (CH1γ4) comprises:
   a) isolating a nucleic acid sequence comprising the CH1 domain of a human-mouse chimeric IgG1 monoclonal antibody, said nucleic acid sequence preferably encoding the heavy chain of the antibody;
   b) substituting said CH1γ1 nucleic acid sequence with a nucleic acid sequence encoding the CH1 domain from a human IgG2 (CH1γ2), IgG3 (CH1γ3) or IgG4 (CH1γ4) to provide a mutated nucleic acid sequence;
   c) providing the mutated nucleic acid sequence with operable expression elements;
   d) co-expressing the mutated nucleic acid with a nucleic acid sequence encoding the light chain of the antibody in a suitable host thereby providing a mutated human-mouse chimeric IgG1 monoclonal antibody, or functional fragment thereof; and
   e) optionally, isolating the mutated antibody, or functional fragment thereof.

7. The method of claim 1, wherein said method further comprises a step of restoring the pairing pattern between the hinge and CH2 domain similar to that existing in human IgG2, IgG3 and IgG4 subclasses by substituting the cysteine residue at the fifth position of the human hinge IgG1 domain from said antibody by another amino acid, or by substituting said human hinge IgG1 domain with the hinge domain of human IgG2, IgG3, IgG4, or a derivative of hinge domain of human IgG3.

8. The method of claim 7, wherein the cysteine residue at the fifth position of the human hinge IgG1 domain from said antibody is substituted by a serine residue.

9. The method of claim 8, wherein the substituting of the cysteine residue at the fifth position of the human hinge IgG1 domain from said antibody by a serine residue comprises:
   a) isolating a nucleic acid sequence comprising the hinge domain of a human-mouse chimeric IgG1 monoclonal antibody, said nucleic acid sequence preferably encoding the heavy chain of the antibody;
   b) mutating the codon encoding the amino acid residue cysteine (C) at position 5 of said human hinge IgG1 domain to encode a serine residue, to provide a mutated nucleic acid sequence;
   c) providing the mutated nucleic acid sequence with operable expression elements;
   d) co-expressing the mutated nucleic acid with a nucleic acid sequence encoding the light chain of the antibody in a suitable host thereby providing a mutated human-mouse chimeric IgG1 monoclonal antibody, or functional fragment thereof; and
   e) optionally, isolating the mutated antibody, or functional fragment thereof.

10. The method of claim 7, wherein the substituting of the human hinge IgG1 domain from said antibody with the hinge domain of human IgG2, IgG3, IgG4, or a derivative of a hinge domain of human IgG3, comprises:
   a) isolating a nucleic acid sequence comprising the hinge domain of a human-mouse chimeric IgG1 monoclonal antibody, said nucleic acid sequence preferably encoding the heavy chain of the antibody;
   b) substituting said human hinge IgG1 domain nucleic acid sequence with a nucleic acid sequence encoding the hinge domain from a human IgG2, IgG3, IgG4 or a derivative of hinge domain of human IgG3 to provide a mutated nucleic acid sequence;
   c) providing the mutated nucleic acid sequence with operable expression elements;
   d) co-expressing the mutated nucleic acid with a nucleic acid sequence encoding the light chain of the antibody in a suitable host thereby providing a mutated human-mouse chimeric IgG1 monoclonal antibody, or functional fragment thereof; and
   e) optionally, isolating the mutated antibody, or functional fragment thereof.

11. The method of claim 7, wherein the increased pro-apoptotic activity of the modified human-mouse chimeric IgG1 monoclonal antibody, or functional fragment thereof results in a higher degree of tumoral antigen bearing tumor cell-depletion as compared to that obtained with a non-modified human-mouse chimeric IgG1 monoclonal antibody having a native CH1γ1 domain, of the same binding specificity under the same binding conditions.

12. The method of claim 1, wherein the tumoral antigen is a ganglioside.

13. The method of claim 7, wherein the tumoral antigen is a ganglioside.

14. A human-mouse chimeric IgG1 monoclonal antibody raised against a tumoral antigen, or functional fragment of said antibody obtained by the method of claim 1, wherein said antibody comprises:
   a) a light chain comprising the following amino acid sequences:
      i) the Light Chain Variable Region (LCVR) specific for a tumoral antigen; and
      ii) a human kappa (K) Constant (CL) domain from a human IgG1 having the sequence of SEQ ID NO: 10; and
   b) a heavy chain comprising the following amino acid sequences:
      i) the Heavy Chain Variable Region (HCVR) specific for said tumoral antigen;
      ii) the CH2 and CH3 domains from a human IgG1 having the sequence of SEQ ID NO: 11; and
      iii) a mutated CH1 domain from a human IgG1, wherein the mutation consists in substituting one amino acid at position 133 or 134 of the human CH1γ1 domain from said antibody by a cysteine residue, or a CH1 domain of human IgG2, IgG3 or IgG4 so as to restore the pairing pattern between CH1 and CL domains similar to that existing in human IgG2, IgG3 and IgG4 subclasses,
   wherein an increased pro-apoptotic activity of the modified human-mouse chimeric IgG1 monoclonal antibody, or functional fragment of said antibody, results in a higher degree of tumoral antigen bearing tumor cell-depletion as compared to that obtained with a non-modified human-mouse chimeric IgG1 monoclonal antibody having a native CH1g1 domain of the same binding specificity under the same binding conditions, and
   wherein the cysteine residue introduced within the CH1 domain do not liberate any free thiol group previously bonded to another cysteine residue anywhere in the antibody molecule.

15. The antibody of claim 14, wherein said human-mouse chimeric IgG1 monoclonal antibody comprises a cysteine residue at the 133 or 134 position of SEQ ID NO: 1 or SEQ ID NO: 22.

16. The antibody of claim 14, wherein said human-mouse chimeric IgG1 monoclonal antibody comprises a CH1 domain of human IgG2 (CH1γ2), IgG3 (CH1γ3), or IgG4 (CH1γ4).

17. The antibody of claim 14, wherein said human-mouse chimeric IgG1 monoclonal antibody also comprises a mutated hinge domain of human IgG1, a hinge domain of human IgG2, IgG3, IgG4 or a derivative of a hinge domain of human IgG3.

18. The antibody of claim 17, wherein the hinge domain of human-mouse chimeric IgG1 monoclonal antibody is mutated by substituting the cysteine residue at the fifth position of its sequence by a serine, so as to restore the pairing pattern between the hinge and the CH2 domain similar to that existing in human IgG2, IgG3 and IgG4 subclasses.

19. The antibody of claim 18, wherein said mutated hinge domain of IgG1 has the sequence SEQ ID NO: 4.

20. The antibody of claim 17, wherein said human-mouse chimeric IgG1 monoclonal antibody comprises the hinge domain of human IgG2, IgG3, IgG4 or a derivative of a hinge domain of human IgG3.

21. The antibody of claim 20, wherein said human-mouse chimeric IgG1 monoclonal antibody comprises the hinge domain of human IgG3 or a derivative of a hinge domain of human IgG3.

22. The antibody of claim 21, wherein said hinge domain of human IgG3 or derivatives thereof is selected from the group consisting of SEQ ID NO: 5, SEQ ID NO: 6, SEQ ID NO: 7, SEQ ID NO: 8 and SEQ ID NO: 9.

23. The antibody of claim 14, wherein said antibody is an immunoconjugate.

24. The antibody of claim 16, wherein said antibody comprises a CH1 domain of human IgG3 (CH1γ3) of SEQ ID NO: 2.

25. A composition comprising at least one antibody as defined in claim 14, and a pharmaceutically acceptable carrier.

* * * * *

SEQUENCE LISTING

```
<160> NUMBER OF SEQ ID NOS: 66

<210> SEQ ID NO 1
<211> LENGTH: 98
<212> TYPE: PRT
<213> ORGANISM: Artificial Sequence
<220> FEATURE:
<223> OTHER INFORMATION: mutated CH1 gamma1

<400> SEQUENCE: 1

Ala Ser Thr Lys Gly Pro Ser Val Phe Pro Leu Ala Pro Cys Ser Lys
1               5                   10                  15
```

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 2
<211> LENGTH: 98
<212> TYPE: PRT
<213> ORGANISM: Homo sapiens

<400> SEQUENCE: 2

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val

<210> SEQ ID NO 3
<211> LENGTH: 15
<212> TYPE: PRT
<213> ORGANISM: Homo sapiens

<400> SEQUENCE: 3

Glu Pro Lys Ser Cys Asp Lys Thr His Thr Cys Pro Pro Cys Pro
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: mutated hinge domain

<400> SEQUENCE: 4

Glu Pro Lys Ser Ser Asp Lys Thr His Thr Cys Pro Pro Cys Pro
1               5                   10                  15

<210> SEQ ID NO 5
<211> LENGTH: 62
<212> TYPE: PRT
<213> ORGANISM: Homo sapiens

<400> SEQUENCE: 5

Glu Leu Lys Thr Pro Leu Gly Asp Thr Thr His Thr Cys Pro Arg Cys
1               5                   10                  15

```
Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro
    50                  55                  60
```

<210> SEQ ID NO 6
<211> LENGTH: 47
<212> TYPE: PRT
<213> ORGANISM: Artificial Sequence
<220> FEATURE:
<223> OTHER INFORMATION: mutated hinge domain

<400> SEQUENCE: 6

```
Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro
        35                  40                  45
```

<210> SEQ ID NO 7
<211> LENGTH: 32
<212> TYPE: PRT
<213> ORGANISM: Artificial Sequence
<220> FEATURE:
<223> OTHER INFORMATION: mutated hinge domain

<400> SEQUENCE: 7

```
Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30
```

<210> SEQ ID NO 8
<211> LENGTH: 15
<212> TYPE: PRT
<213> ORGANISM: Artificial Sequence
<220> FEATURE:
<223> OTHER INFORMATION: mutated hinge domain

<400> SEQUENCE: 8

```
Glu Pro Lys Ser Cys Asp Thr Pro Pro Cys Pro Arg Cys Pro
1               5                   10              15
```

<210> SEQ ID NO 9
<211> LENGTH: 17
<212> TYPE: PRT
<213> ORGANISM: Artificial Sequence
<220> FEATURE:
<223> OTHER INFORMATION: mutated hinge domain

<400> SEQUENCE: 9

```
Glu Leu Lys Thr Pro Leu Gly Asp Thr Thr His Thr Cys Pro Arg Cys
1               5                   10                  15

Pro
```

<210> SEQ ID NO 10
<211> LENGTH: 107
<212> TYPE: PRT
<213> ORGANISM: Homo sapiens

<400> SEQUENCE: 10

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 11
<211> LENGTH: 217
<212> TYPE: PRT
<213> ORGANISM: Homo sapiens

<400> SEQUENCE: 11

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 12
<211> LENGTH: 219
<212> TYPE: PRT
<213> ORGANISM: Artificial Sequence
<220> FEATURE:

<223> OTHER INFORMATION: chimerized light chain

<400> SEQUENCE: 12

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Lys Asn
            20                  25                  30

Asn Gly Asn Thr Phe Leu His Trp Tyr Leu Gln Lys Ser Gly Gln Ser
        35                  40                  45

Pro Lys Leu Leu Ile Tyr Lys Val Ser Asn Arg Leu Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
                85                  90                  95

Thr His Ile Pro Tyr Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 13
<211> LENGTH: 449
<212> TYPE: PRT
<213> ORGANISM: Artificial Sequence
<220> FEATURE:
<223> OTHER INFORMATION: chimerized heavy chain

<400> SEQUENCE: 13

Glu Val Lys Leu Val Glu Ser Gly Gly Gly Leu Val Leu Pro Gly Asp
1               5                   10                  15

Ser Leu Arg Leu Ser Cys Ala Thr Ser Glu Phe Thr Phe Thr Asp Tyr
            20                  25                  30

Tyr Met Thr Trp Val Arg Gln Pro Pro Arg Lys Ala Leu Glu Trp Leu
        35                  40                  45

Gly Phe Ile Arg Asn Arg Ala Asn Gly Tyr Thr Thr Glu Tyr Asn Pro
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Thr Glu Asp Ser Ala Thr Tyr
                85                  90                  95

Tyr Cys Ala Arg Val Ser Asn Trp Ala Phe Asp Tyr Trp Gly Gln Gly
            100                 105                 110

Thr Thr Leu Thr Val Ser Ser Ala Ser Thr Lys Gly Pro Ser Val Phe
        115                 120                 125

```
Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 14
<211> LENGTH: 121
<212> TYPE: PRT
<213> ORGANISM: Artificial Sequence
<220> FEATURE:
<223> OTHER INFORMATION: Ab 301.14a

<400> SEQUENCE: 14

Ala Ser Thr Lys Gly Pro Ser Val Phe Pro Leu Ala Pro Cys Ser Lys
1               5                   10                  15

Ser Thr Ser Gly Gly Thr Ala Ala Leu Gly Cys Leu Val Lys Asp Tyr
                20                  25                  30
```

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro
            115                 120

<210> SEQ ID NO 15
<211> LENGTH: 121
<212> TYPE: PRT
<213> ORGANISM: Artificial Sequence
<220> FEATURE:
<223> OTHER INFORMATION: Ab 301.14b

<400> SEQUENCE: 15

Ala Ser Thr Lys Gly Pro Ser Val Phe Pro Leu Ala Pro Cys Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                85                  90                  95

Lys Val Glu Pro Lys Ser Ser Asp Lys Thr His Thr Cys Pro Pro Cys
            100                 105                 110

Pro Ala Pro Glu Leu Leu Gly Gly Pro
            115                 120

<210> SEQ ID NO 16
<211> LENGTH: 121
<212> TYPE: PRT
<213> ORGANISM: Artificial Sequence
<220> FEATURE:
<223> OTHER INFORMATION: Ab 301.15

<400> SEQUENCE: 16

Ala Ser Thr Lys Gly Pro Ser Val Phe Pro Leu Ala Pro Cys Ser Arg
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
 65                  70                  75                  80

Tyr Thr Cys Asn Val Asn His Lys Pro Ser Asn Thr Lys Val Asp Lys
                85                  90                  95

```
Arg Val Glu Pro Lys Ser Cys Asp Lys Thr His Thr Cys Pro Pro Cys
            100                 105                 110

Pro Ala Pro Glu Leu Leu Gly Gly Pro
            115                 120
```

<210> SEQ ID NO 17
<211> LENGTH: 168
<212> TYPE: PRT
<213> ORGANISM: Artificial Sequence
<220> FEATURE:
<223> OTHER INFORMATION: Ab 301.16

<400> SEQUENCE: 17

```
Ala Ser Thr Lys Gly Pro Ser Val Phe Pro Leu Ala Pro Cys Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
145                 150                 155                 160

Ala Pro Glu Leu Leu Gly Gly Pro
                165
```

<210> SEQ ID NO 18
<211> LENGTH: 168
<212> TYPE: PRT
<213> ORGANISM: Artificial Sequence
<220> FEATURE:
<223> OTHER INFORMATION: Ab 301.17

<400> SEQUENCE: 18

```
Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
```

```
              100                 105                 110
Arg Cys Pro Glu Pro Lys Ser Cys Asp Thr Pro Pro Cys Pro Arg
            115                 120                 125

Cys Pro Glu Pro Lys Ser Cys Asp Thr Pro Pro Cys Pro Arg Cys
        130                 135                 140

Pro Glu Pro Lys Ser Cys Asp Thr Pro Pro Cys Pro Arg Cys Pro
145                 150                 155                 160

Ala Pro Glu Leu Leu Gly Gly Pro
                165

<210> SEQ ID NO 19
<211> LENGTH: 123
<212> TYPE: PRT
<213> ORGANISM: Artificial Sequence
<220> FEATURE:
<223> OTHER INFORMATION: Ab 301.18

<400> SEQUENCE: 19

Ala Ser Thr Lys Gly Pro Ser Val Phe Pro Leu Ala Pro Cys Ser Lys
1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Leu Lys Thr Pro Leu Gly Asp Thr Thr His Thr Cys Pro
            100                 105                 110

Arg Cys Pro Ala Pro Glu Leu Leu Gly Gly Pro
            115                 120

<210> SEQ ID NO 20
<211> LENGTH: 123
<212> TYPE: PRT
<213> ORGANISM: Artificial Sequence
<220> FEATURE:
<223> OTHER INFORMATION: Ab 301.19

<400> SEQUENCE: 20

Ala Ser Thr Lys Gly Pro Ser Val Phe Pro Leu Ala Pro Cys Ser Arg
1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110
```

```
Arg Cys Pro Ala Pro Glu Leu Leu Gly Gly Pro
        115                 120
```

<210> SEQ ID NO 21
<211> LENGTH: 98
<212> TYPE: PRT
<213> ORGANISM: Artificial Sequence
<220> FEATURE:
<223> OTHER INFORMATION: wild type human CH1 gamma1

<400> SEQUENCE: 21

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val
```

<210> SEQ ID NO 22
<211> LENGTH: 98
<212> TYPE: PRT
<213> ORGANISM: Artificial Sequence
<220> FEATURE:
<223> OTHER INFORMATION: mutated human CH1 gamma1

<400> SEQUENCE: 22

```
Ala Ser Thr Lys Gly Pro Ser Val Phe Pro Leu Ala Pro Ser Cys Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val
```

<210> SEQ ID NO 23
<211> LENGTH: 113
<212> TYPE: PRT
<213> ORGANISM: Artificial Sequence
<220> FEATURE:
<223> OTHER INFORMATION: human CH1 gamma2

<400> SEQUENCE: 23

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Pro Lys Ser Cys Asp Lys Thr His Thr Cys Pro Pro Cys
            100                 105                 110

Pro

<210> SEQ ID NO 24
<211> LENGTH: 113
<212> TYPE: PRT
<213> ORGANISM: Artificial Sequence
<220> FEATURE:
<223> OTHER INFORMATION: human CH1 gamma4

<400> SEQUENCE: 24

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro

<210> SEQ ID NO 25
<211> LENGTH: 25
<212> TYPE: PRT
<213> ORGANISM: Artificial Sequence
<220> FEATURE:
<223> OTHER INFORMATION: FR1 HC

<400> SEQUENCE: 25

Gln Val Gln Leu Gln Gln Pro Gly Ala Glu Leu Val Lys Pro Gly Ala
 1               5                  10                  15

Ser Val Lys Met Ser Cys Lys Ala Ser
            20                  25

<210> SEQ ID NO 26
<211> LENGTH: 8
<212> TYPE: PRT
<213> ORGANISM: Artificial Sequence
<220> FEATURE:
<223> OTHER INFORMATION: CDR1 HC

<400> SEQUENCE: 26

Gly Tyr Thr Phe Thr Ser Tyr Asn
 1               5
```

```
<210> SEQ ID NO 27
<211> LENGTH: 17
<212> TYPE: PRT
<213> ORGANISM: Artificial Sequence
<220> FEATURE:
<223> OTHER INFORMATION: FR2 HC

<400> SEQUENCE: 27

Met His Trp Val Lys Gln Thr Pro Gly Arg Gly Leu Glu Trp Ile Gly
1               5                   10                  15

Ala

<210> SEQ ID NO 28
<211> LENGTH: 8
<212> TYPE: PRT
<213> ORGANISM: Artificial Sequence
<220> FEATURE:
<223> OTHER INFORMATION: CDR2 HC

<400> SEQUENCE: 28

Ile Tyr Pro Gly Asn Gly Asp Thr
1               5

<210> SEQ ID NO 29
<211> LENGTH: 38
<212> TYPE: PRT
<213> ORGANISM: Artificial Sequence
<220> FEATURE:
<223> OTHER INFORMATION: FR3 HC

<400> SEQUENCE: 29

Ser Tyr Asn Gln Lys Phe Lys Gly Lys Ala Thr Leu Thr Ala Asp Lys
1               5                   10                  15

Ser Ser Ser Thr Ala Tyr Met Gln Leu Ser Ser Leu Thr Ser Glu Asp
            20                  25                  30

Ser Ala Val Tyr Tyr Cys
        35

<210> SEQ ID NO 30
<211> LENGTH: 14
<212> TYPE: PRT
<213> ORGANISM: Artificial Sequence
<220> FEATURE:
<223> OTHER INFORMATION: CDR3 HC

<400> SEQUENCE: 30

Ala Arg Ser Thr Tyr Tyr Gly Gly Asp Trp Tyr Phe Asn Val
1               5                   10

<210> SEQ ID NO 31
<211> LENGTH: 11
<212> TYPE: PRT
<213> ORGANISM: Artificial Sequence
<220> FEATURE:
<223> OTHER INFORMATION: FR4 HC

<400> SEQUENCE: 31

Trp Gly Ala Gly Thr Thr Val Thr Val Ser Ala
1               5                   10

<210> SEQ ID NO 32
<211> LENGTH: 25
<212> TYPE: PRT
<213> ORGANISM: Artificial Sequence
<220> FEATURE:
```

-continued

<223> OTHER INFORMATION: FR1 LC

<400> SEQUENCE: 32

Gln Ile Val Leu Ser Gln Ser Pro Ala Ile Leu Ser Ala Ser Pro Gly
1               5                   10                  15

Glu Lys Val Thr Met Thr Cys Arg Ala
            20                  25

<210> SEQ ID NO 33
<211> LENGTH: 5
<212> TYPE: PRT
<213> ORGANISM: Artificial Sequence
<220> FEATURE:
<223> OTHER INFORMATION: CDR1 LC

<400> SEQUENCE: 33

Ser Ser Val Ser Tyr
1               5

<210> SEQ ID NO 34
<211> LENGTH: 17
<212> TYPE: PRT
<213> ORGANISM: Artificial Sequence
<220> FEATURE:
<223> OTHER INFORMATION: FR2 LC

<400> SEQUENCE: 34

Ile His Trp Phe Gln Gln Lys Pro Gly Ser Ser Pro Lys Pro Trp Ile
1               5                   10                  15

Tyr

<210> SEQ ID NO 35
<211> LENGTH: 36
<212> TYPE: PRT
<213> ORGANISM: Artificial Sequence
<220> FEATURE:
<223> OTHER INFORMATION: FR3 LC

<400> SEQUENCE: 35

Asn Leu Ala Ser Gly Val Pro Val Arg Phe Ser Gly Ser Gly Ser Gly
1               5                   10                  15

Thr Ser Tyr Ser Leu Thr Ile Ser Arg Val Glu Ala Glu Asp Ala Ala
            20                  25                  30

Thr Tyr Tyr Cys
        35

<210> SEQ ID NO 36
<211> LENGTH: 9
<212> TYPE: PRT
<213> ORGANISM: Artificial Sequence
<220> FEATURE:
<223> OTHER INFORMATION: CDR3 LC

<400> SEQUENCE: 36

Gln Gln Trp Thr Ser Asn Pro Pro Thr
1               5

<210> SEQ ID NO 37
<211> LENGTH: 10
<212> TYPE: PRT
<213> ORGANISM: Artificial Sequence
<220> FEATURE:
<223> OTHER INFORMATION: FR4 LC

<400> SEQUENCE: 37

```
Phe Gly Gly Gly Thr Lys Leu Glu Ile Lys
1               5                   10
```

<210> SEQ ID NO 38
<211> LENGTH: 112
<212> TYPE: PRT
<213> ORGANISM: Artificial Sequence
<220> FEATURE:
<223> OTHER INFORMATION: CH1 and hinge domains

<400> SEQUENCE: 38

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110
```

<210> SEQ ID NO 39
<211> LENGTH: 25
<212> TYPE: PRT
<213> ORGANISM: Artificial Sequence
<220> FEATURE:
<223> OTHER INFORMATION: FR1 HC

<400> SEQUENCE: 39

```
Glu Val Gln Leu Val Glu Ser Gly Gly Gly Leu Val Gln Pro Gly Gly
1               5                   10                  15

Ser Leu Arg Leu Ser Cys Ala Ala Ser
                20                  25
```

<210> SEQ ID NO 40
<211> LENGTH: 8
<212> TYPE: PRT
<213> ORGANISM: Artificial Sequence
<220> FEATURE:
<223> OTHER INFORMATION: CDR1 HC

<400> SEQUENCE: 40

```
Gly Phe Asn Ile Lys Asp Thr Tyr
1               5
```

<210> SEQ ID NO 41
<211> LENGTH: 17
<212> TYPE: PRT
<213> ORGANISM: Artificial Sequence
<220> FEATURE:
<223> OTHER INFORMATION: FR2 HC

<400> SEQUENCE: 41

```
Ile His Trp Val Arg Gln Ala Pro Gly Lys Gly Leu Glu Trp Val Ala
1               5                   10                  15

Arg
```

<210> SEQ ID NO 42
<211> LENGTH: 8
<212> TYPE: PRT
<213> ORGANISM: Artificial Sequence
<220> FEATURE:
<223> OTHER INFORMATION: CDR2 HC

<400> SEQUENCE: 42

Ile Tyr Pro Thr Asn Gly Tyr Thr
1               5

<210> SEQ ID NO 43
<211> LENGTH: 38
<212> TYPE: PRT
<213> ORGANISM: Artificial Sequence
<220> FEATURE:
<223> OTHER INFORMATION: FR3 HC

<400> SEQUENCE: 43

Arg Tyr Ala Asp Ser Val Lys Gly Arg Phe Thr Ile Ser Ala Asp Thr
1               5                   10                  15

Ser Lys Asn Thr Ala Tyr Leu Gln Met Asn Ser Leu Arg Ala Glu Asp
            20                  25                  30

Thr Ala Val Tyr Tyr Cys
        35

<210> SEQ ID NO 44
<211> LENGTH: 13
<212> TYPE: PRT
<213> ORGANISM: Artificial Sequence
<220> FEATURE:
<223> OTHER INFORMATION: CDR3 HC

<400> SEQUENCE: 44

Ser Arg Trp Gly Gly Asp Gly Phe Tyr Ala Met Asp Tyr
1               5                   10

<210> SEQ ID NO 45
<211> LENGTH: 11
<212> TYPE: PRT
<213> ORGANISM: Artificial Sequence
<220> FEATURE:
<223> OTHER INFORMATION: FR4 HC

<400> SEQUENCE: 45

Trp Gly Gln Gly Thr Leu Val Thr Val Ser Ser
1               5                   10

<210> SEQ ID NO 46
<211> LENGTH: 26
<212> TYPE: PRT
<213> ORGANISM: Artificial Sequence
<220> FEATURE:
<223> OTHER INFORMATION: FR1 LC

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser
            20                  25

<210> SEQ ID NO 47
<211> LENGTH: 6
<212> TYPE: PRT
<213> ORGANISM: Artificial Sequence

```
<220> FEATURE:
<223> OTHER INFORMATION: CDR1 LC

<400> SEQUENCE: 47

Gln Asp Val Asn Thr Ala
1               5

<210> SEQ ID NO 48
<211> LENGTH: 17
<212> TYPE: PRT
<213> ORGANISM: Artificial Sequence
<220> FEATURE:
<223> OTHER INFORMATION: FR2 LC

<400> SEQUENCE: 48

Val Ala Trp Tyr Gln Gln Lys Pro Gly Lys Ala Pro Lys Leu Leu Ile
1               5                   10                  15

Tyr

<210> SEQ ID NO 49
<211> LENGTH: 36
<212> TYPE: PRT
<213> ORGANISM: Artificial Sequence
<220> FEATURE:
<223> OTHER INFORMATION: FR3 LC

<400> SEQUENCE: 49

Phe Leu Tyr Ser Gly Val Pro Ser Arg Phe Ser Gly Ser Arg Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35

<210> SEQ ID NO 50
<211> LENGTH: 9
<212> TYPE: PRT
<213> ORGANISM: Artificial Sequence
<220> FEATURE:
<223> OTHER INFORMATION: CDR3 LC

<400> SEQUENCE: 50

Gln Gln His Tyr Thr Thr Pro Pro Thr
1               5

<210> SEQ ID NO 51
<211> LENGTH: 10
<212> TYPE: PRT
<213> ORGANISM: Artificial Sequence
<220> FEATURE:
<223> OTHER INFORMATION: FR4 LC

<400> SEQUENCE: 51

Phe Gly Gln Gly Thr Lys Val Glu Ile Lys
1               5                   10

<210> SEQ ID NO 52
<211> LENGTH: 25
<212> TYPE: PRT
<213> ORGANISM: Artificial Sequence
<220> FEATURE:
<223> OTHER INFORMATION: FR1 HC

<400> SEQUENCE: 52

Glu Val Gln Leu Leu Gln Ser Gly Pro Glu Leu Glu Lys Pro Gly Ala
```

```
1               5                   10                  15
Ser Val Met Ile Ser Cys Lys Ala Ser
            20                  25
```

<210> SEQ ID NO 53
<211> LENGTH: 8
<212> TYPE: PRT
<213> ORGANISM: Artificial Sequence
<220> FEATURE:
<223> OTHER INFORMATION: CDR1 HC

<400> SEQUENCE: 53

```
Gly Ser Ser Phe Thr Gly Tyr Asn
1               5
```

<210> SEQ ID NO 54
<211> LENGTH: 17
<212> TYPE: PRT
<213> ORGANISM: Artificial Sequence
<220> FEATURE:
<223> OTHER INFORMATION: FR2 HC

<400> SEQUENCE: 54

```
Met Asn Trp Val Arg Gln Asn Ile Gly Lys Ser Leu Glu Trp Ile Gly
1               5                   10                  15
Ala
```

<210> SEQ ID NO 55
<211> LENGTH: 8
<212> TYPE: PRT
<213> ORGANISM: Artificial Sequence
<220> FEATURE:
<223> OTHER INFORMATION: CDR2 HC

<400> SEQUENCE: 55

```
Ile Asp Pro Tyr Tyr Gly Gly Thr
1               5
```

<210> SEQ ID NO 56
<211> LENGTH: 38
<212> TYPE: PRT
<213> ORGANISM: Artificial Sequence
<220> FEATURE:
<223> OTHER INFORMATION: FR3 HC

<400> SEQUENCE: 56

```
Ser Tyr Asn Gln Lys Phe Lys Gly Arg Ala Thr Leu Thr Val Asp Lys
1               5                   10                  15
Ser Ser Ser Thr Ala Tyr Met His Leu Lys Ser Leu Thr Ser Glu Asp
            20                  25                  30
Ser Ala Val Tyr Tyr Cys
            35
```

<210> SEQ ID NO 57
<211> LENGTH: 6
<212> TYPE: PRT
<213> ORGANISM: Artificial Sequence
<220> FEATURE:
<223> OTHER INFORMATION: CDR3 HC

<400> SEQUENCE: 57

```
Val Ser Gly Met Glu Tyr
1               5
```

```
<210> SEQ ID NO 58
<211> LENGTH: 11
<212> TYPE: PRT
<213> ORGANISM: Artificial Sequence
<220> FEATURE:
<223> OTHER INFORMATION: FR4 HC

<400> SEQUENCE: 58

Trp Gly Gln Gly Thr Ser Val Thr Val Ser Ser
1               5                   10

<210> SEQ ID NO 59
<211> LENGTH: 26
<212> TYPE: PRT
<213> ORGANISM: Artificial Sequence
<220> FEATURE:
<223> OTHER INFORMATION: FR1 LC

<400> SEQUENCE: 59

Asp Val Val Met Thr Gln Thr Pro Leu Ser Leu Pro Ile Ser Leu Gly
1               5                   10                  15

Asp Gln Ala Ser Ile Ser Cys Arg Ser Ser
            20                  25

<210> SEQ ID NO 60
<211> LENGTH: 12
<212> TYPE: PRT
<213> ORGANISM: Artificial Sequence
<220> FEATURE:
<223> OTHER INFORMATION: CDR1 LC

<400> SEQUENCE: 60

Gln Ser Leu Val His Arg Asn Gly Asn Thr Tyr Leu
1               5                   10

<210> SEQ ID NO 61
<211> LENGTH: 16
<212> TYPE: PRT
<213> ORGANISM: Artificial Sequence
<220> FEATURE:
<223> OTHER INFORMATION: FR2 LC

<400> SEQUENCE: 61

His Trp Tyr Leu Gln Lys Pro Gly Gln Ser Pro Lys Leu Leu Ile His
1               5                   10                  15

<210> SEQ ID NO 62
<211> LENGTH: 36
<212> TYPE: PRT
<213> ORGANISM: Artificial Sequence
<220> FEATURE:
<223> OTHER INFORMATION: FR3 LC

<400> SEQUENCE: 62

Asn Arg Phe Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Leu Gly
            20                  25                  30

Val Tyr Phe Cys
        35

<210> SEQ ID NO 63
<211> LENGTH: 10
<212> TYPE: PRT
<213> ORGANISM: Artificial Sequence
<220> FEATURE:
```

<223> OTHER INFORMATION: CDR3 LC

<400> SEQUENCE: 63

Ser Gln Ser Thr His Val Pro Pro Leu Thr
1               5                   10

<210> SEQ ID NO 64
<211> LENGTH: 10
<212> TYPE: PRT
<213> ORGANISM: Artificial Sequence
<220> FEATURE:
<223> OTHER INFORMATION: FR4 LC

<400> SEQUENCE: 64

Phe Gly Ala Gly Thr Lys Leu Glu Leu Asn
1               5                   10

<210> SEQ ID NO 65
<211> LENGTH: 113
<212> TYPE: PRT
<213> ORGANISM: Artificial Sequence
<220> FEATURE:
<223> OTHER INFORMATION: Murine IgG3 and inverse mutant CH1 and Hinge
      sequence

<400> SEQUENCE: 65

Ala Thr Thr Thr Ala Pro Ser Val Tyr Pro Leu Val Pro Gly Cys Ser
1               5                   10                  15

Asp Thr Ser Gly Ser Ser Val Thr Leu Gly Cys Leu Val Lys Gly Tyr
                20                  25                  30

Phe Pro Glu Pro Val Thr Val Lys Trp Asn Tyr Gly Ala Leu Ser Ser
            35                  40                  45

Gly Val Arg Thr Val Ser Ser Val Leu Gln Ser Gly Phe Tyr Ser Leu
        50                  55                  60

Ser Ser Leu Val Thr Val Pro Ser Ser Thr Trp Pro Ser Gln Thr Val
65                  70                  75                  80

Ile Cys Asn Val Ala His Pro Ala Ser Lys Thr Glu Leu Ile Lys Arg
                85                  90                  95

Ile Glu Pro Arg Ile Pro Lys Pro Cys Thr Pro Pro Gly Ser Ser Cys
            100                 105                 110

Pro

<210> SEQ ID NO 66
<211> LENGTH: 113
<212> TYPE: PRT
<213> ORGANISM: Artificial Sequence
<220> FEATURE:
<223> OTHER INFORMATION: Ab 301.15b

<400> SEQUENCE: 66

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

-continued

```
Tyr Thr Cys Asn Val Asn His Lys Pro Ser Asn Thr Lys Val Asp Lys
                85              90                  95

Arg Val Glu Pro Lys Ser Ser Asp Lys Thr His Thr Cys Pro Pro Cys
            100             105             110

Pro
```